US011046976B2

(12) United States Patent
Wu

(10) Patent No.: US 11,046,976 B2
(45) Date of Patent: *Jun. 29, 2021

(54) MECHANICAL TRANSFECTION DEVICES AND METHODS

(71) Applicant: NanoCav, LLC, Culver City, CA (US)

(72) Inventor: Ting Wu, Culver City, CA (US)

(73) Assignee: NanoCav, LLC, Culver City, CA (US)

( * ) Notice: Subject to any disclaimer, the term of this patent is extended or adjusted under 35 U.S.C. 154(b) by 270 days.

This patent is subject to a terminal disclaimer.

(21) Appl. No.: 16/139,722

(22) Filed: Sep. 24, 2018

(65) Prior Publication Data

US 2019/0127761 A1 May 2, 2019

Related U.S. Application Data

(63) Continuation of application No. 14/852,433, filed on Sep. 11, 2015, now Pat. No. 10,081,816, which is a continuation-in-part of application No. 14/754,625, filed on Jun. 29, 2015, now Pat. No. 10,760,040.

(60) Provisional application No. 62/049,747, filed on Sep. 12, 2014, provisional application No. 62/020,910, filed on Jul. 3, 2014.

(51) Int. Cl.
    *C12N 15/87* (2006.01)

(52) U.S. Cl.
    CPC .................... *C12N 15/87* (2013.01)

(58) Field of Classification Search
    CPC ........ C12N 15/87; C12N 15/89; C12N 13/00; C12N 2521/00; C12M 35/04; C12M 33/04; C12M 41/40; B01L 3/50273; A61M 5/1452
    See application file for complete search history.

(56) References Cited

U.S. PATENT DOCUMENTS

| 5,586,982 A | 12/1996 | Abela |
| 5,853,663 A | 12/1998 | Wittig et al. |
| 5,922,687 A | 7/1999 | Mann |
| 6,071,276 A | 6/2000 | Abela |

(Continued)

FOREIGN PATENT DOCUMENTS

| EP | 1818399 A1 | 8/2007 |
| WO | 1996024360 A1 | 8/1996 |

(Continued)

OTHER PUBLICATIONS

Shi, J., et al., "Pressure Regulated Biornolecule injection into NIH 3T3 Cells Through Integrated Nano/Mesopores," 14th Int'l Conference on Miniaturized Systems for Chemistry and Life Sciences, pp. 491-493 (2010).

(Continued)

*Primary Examiner* — Arthur S Leonard
(74) *Attorney, Agent, or Firm* — Harness, Dickey & Pierce, P.L.C.

(57) ABSTRACT

Systems and methods for transfection devices are contemplated for delivery of various complex macrostructures. Preferred systems and methods are suitable for mRNA reprogramming and genome editing and use mechanical force to induce uptake of the macrostructures in a target cell. Contemplated devices are able to achieve high throughput of transfected cells in remarkably short time that remain viable and are capable of producing colonies.

19 Claims, 15 Drawing Sheets

Single Well Side View of Deformable Fluid Reservoir

(56) References Cited

U.S. PATENT DOCUMENTS

| | | |
|---|---|---|
| 6,190,380 B1 | 2/2001 | Abela |
| 6,367,343 B1 | 4/2002 | Balamucki et al. |
| 6,408,878 B2 | 6/2002 | Unger et al. |
| 7,687,267 B2 | 3/2010 | Huang |
| 8,367,343 B2 | 2/2013 | Huang |
| 8,507,265 B2 | 8/2013 | Huang |
| 8,513,000 B2 | 8/2013 | Huang |
| 9,963,739 B2 | 5/2018 | Kornilovich et al. |
| 10,081,816 B1 | 9/2018 | Wu |
| 10,150,947 B2 * | 12/2018 | Vandersarl ........... C12N 5/0068 |
| 2004/0023850 A1 | 2/2004 | Wolff |
| 2004/0106567 A1 | 6/2004 | Hagstrom |
| 2008/0248575 A1 | 10/2008 | Lee et al. |
| 2009/0081750 A1 | 3/2009 | Ragsdale et al. |
| 2011/0117648 A1 | 5/2011 | Chiou et al. |
| 2011/0165664 A1 | 7/2011 | Fujita et al. |
| 2011/0198221 A1 | 8/2011 | Angelescu |
| 2012/0244593 A1 | 9/2012 | Huang et al. |
| 2013/0166378 A1 | 6/2013 | Musgrove et al. |
| 2013/0216503 A1 | 8/2013 | Srivastava |
| 2014/0179770 A1 * | 6/2014 | Zhang ...................... A61P 3/06 514/44 R |
| 2017/0175139 A1 | 6/2017 | Wu et al. |

FOREIGN PATENT DOCUMENTS

| | | | |
|---|---|---|---|
| WO | 2002042447 A3 | 5/2002 | |
| WO | 2002058847 A3 | 8/2002 | |
| WO | 2013059343 A1 | 4/2013 | |
| WO | 2013166378 A1 | 11/2013 | |

OTHER PUBLICATIONS

Office Action dated Oct. 3, 2019 issued in U.S. Appl. No. 14/754,625, 16 pages.

Freshney, Chapter 1, Basic Principles of Cell Culture, pp. 3-21, from Culture of Cells for Tissue Engineering, ed Vunjak-Novakovic et al., John Wiley & Sons, 2006. (Year: 2006).

Andersen et al., Endothelial Cells Are Susceptible to Rapid siRNA Transfection and Gene Silencing Ex Vivo. J Vasc Surg. Dec. 2010; 52(6): 1608-1615.

Mann et al., Pressure-mediated oligonucleotide transfection of rat and human cardiovascular tissues. Proc. Natl. Acad. Sci. USA. vol. 96, pp. 6411-6416, May 1999.

Kim et al., Ultrasound-Mediated Transfection of Mammalian Cells. Human Gene Therapy 7:1339-1346 (Jul. 10, 1996).

Burgstaller et al., Multiplex Profiling of Cellular Invasion in 3D Cell Culture Models. PLOS One, 2013, 8:1-9.

Mandal et al., Reprogramming human fibroblasts to pluripotency using modified mRNA. Nature Protocols, 2013, 8:586-582.

McCreery et al., DNA Delivery to Cells in Culture Using Ultrasound. Methods Mol Biol. 2004;245:287-92.

Simara et al., Pluripotent Stem Cells and Gene Therapy. Transl Res. Apr. 2013; 161(4): 284-292.

Greiner Bio-One, Product Data Sheet, ThinCert, Tissue Culture Inserts for Multiwell Plates, Mar. 2013, p. 1.

Shen et al., Ultrasound with microbubbles enhances gene expression of plasmid DNA in the liver via intraportal delivery, National Institutes of Health, 15(16), Aug. 2008, pp. 1147-1155.

Ziauddin et al., Microarrays of cells expressing defined cDNAs, Letters to Nature, vol. 411, May 3, 2001, pp. 107-110.

Lonza, Nucleofector Technology, Stretching Transfection Dimensions, www.lonza.com, pp. 1-20 , 2015.

Luo et al., Synthetic DNA delivery systems, Nature Biotechnology, vol. 18, Jan. 2000, pp. 33-37.

Mann et al., Pressure-mediated oligonucleotide transfection of rat and human cardiovascular tissues, Proc. Natl. cad., vol. 96, May 1999, pp. 6411-6416.

Cochran et al., In vitro gene delivery with ultrasound triggered polymer microbubbles, National Institutes of Health, 9(6), Jun. 2013, pp. 1102-1119.

Office Action dated Jul. 11, 2019 issued in U.S. Appl. No. 14/754,625, 14 pages.

Office Action dated Jul. 13, 2018 issued in U.S. Appl. No. 14/754,625, 11 pages.

Office Action dated Sep. 20, 2017 issued in U.S. Appl. No. 14/754,625, 14 pages.

Office Action dated Nov. 23, 2018 issued in U.S. Appl. No. 14/754,625, 10 pages.

Office Action dated Sep. 6, 2016 issued in U.S. Appl. No. 14/852,433, 14 pages.

Office Action dated Mar. 22, 2017 issued in U.S. Appl. No. 14/852,433, 13 pages.

Office Action dated Jun. 9, 2017 issued in U.S. Appl. No. 14/852,433, 8 pages.

Office Action dated Oct. 18, 2017 issued in U.S. Appl. No. 14/852,433, 14 pages.

* cited by examiner

Single Well Side View of Deformable Fluid Reservoir

Scale bar = 100 μm

MECHANICAL TRANSFECTION DEVICES AND METHODS

This application is a continuation of U.S. application Ser. No. 14/852,433, filed Sep. 11, 2015, which is a continuation-in-part application of U.S. application with the Ser. No. 14/754,625, filed Jun. 29, 2015, which claims priority to the U.S. provisional application with Ser. No. 62/020,910, filed Jul. 3, 2014. This application further claims priority to U.S. provisional application with Ser. No. 62/049,747, filed Sep. 12, 2014.

FIELD OF THE INVENTION

The field of the invention is cellular cargo delivery technologies and methods therefor.

BACKGROUND

The background description includes information that may be useful in understanding the present invention. It is not an admission that any of the information provided herein is prior art or relevant to the presently claimed invention, or that any publication specifically or implicitly referenced is prior art.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Transfection processes are used to deliver various types of materials into a cell, and there are numerous known methods in the art. For example, U.S. Pat. No. 5,586,982 describes a treatment device capable of delivering genetic material or drugs into cells of a patient in vivo using heat to assist with transfection. Unfortunately, such approach often tends to damage the cells. Moreover, since the poration lasts only for a very short time, the amount of material delivered into the cells will in most cases be significantly reduced, especially where the material is relatively large. Finally, such approach also fails to provide a method for culturing cells after transfection.

In another example, as described in US 2009/0081750, magnetic fields are employed to move cells through a channel in which the cells undergo transfection. Actual transfection is then performed via several possible manners, including electroporation, heat, or light. Similar to the '982 reference, effective transfection is typically limited to relatively small molecules and low quantities. Yet another example of poration to transfect cells is described in WO 2013/059343. Here, cells are fed through a microfluidic channel in a buffer that contains a delivery material. The cells pass through a constriction region, which causes the cells to become perturbed with pores through which the delivery material then diffuses. While this approach overcomes to at least some degree issues associated with short pulse time, delivery still requires poration.

A more extreme approach is presented in U.S. Pat. No. 5,858,663 in which a cold gas shockwave is used to accelerate micro projectiles that carry matter into the cells. While such approach guarantees delivery of even relatively large molecules into a cell, it is readily apparent that such approach is also prone to significantly damage a cell.

WO 96/24360 attempts to overcome shockwave damage by providing a time-dependent impulse transient characterized by rise time and magnitude that is thought to increase the overall permeability of a cell membrane, which results in an increase in diffusion of materials into the cell. The impulse is achieved by applying an optical field to a film on which the cells are grown, and the optical field ablates the film thereby delivering the impulse. While such approach will provide for transfection, high throughput production of transfected cells remains problematic. To increase throughput, WO 02/42447 teaches use of leverages shock or other forms of pressure, and U.S. Pat. No. 7,687,267 describes a high throughput cell transfection device for transfer of small nucleic acid molecules (e.g., DNA, siRNA) through electroporation where the device contains an array of cell transfection units. Similarly, US 2012/0244593 teaches a high throughput electroporation transfection device, which requires poration (i.e., electroporation) and diffusion to deliver the material.

Unfortunately, the known transfection devices require significant disruption to a cellular membrane to allow for greater diffusion of cargo material, which becomes especially difficult where the cargo material is relatively large. For example, clustered, regularly interspaced, short palindromic repeat (CRISPR) technology has emerged as an important tool for performing targeted and highly-efficient editing of a cell's endogenous genome as evidenced by Cong, L. et al. "Multiplex Genome Engineering Using CRISPR/Cas Systems", *Science* 339, 819-823 (2013); and Ran, F. A. et al. "Genome engineering using the CRISPR-Cas9 system", *Nature Protocols* 8, 2281-2308 (2013). The two essential components of CRISPR technology are a guide RNA and a RNA-guided nuclease, e.g. Cas9. The guide RNA specifies the targeted DNA sequence while recruiting the Cas9 nuclease to the target site for gene editing. Advantageously, multiple genes can be targeted simultaneously by delivering a multiplex of different guide RNA sequences.

One especially desirable use of such complex gene editing is the generation of induced pluripotent stem (iPS) by co-expressing of a cocktail of transcription factors in differentiated somatic cells to so reprogram the cells into a pluripotent state (see e.g., Takahashi, K. & Yamanaka, S. "Induction of pluripotent stem cells from mouse embryonic and adult fibroblast cultures by defined factors", *Cell* 126, 663-676 (2006)). Using mRNAs encoding the respective reprogramming factors, iPS cells can be generated without leaving a genetic footprint in the reprogrammed cells with higher efficiency compared to other DNA-based approaches as indicated by Warren, L. et al. "Highly Efficient Reprogramming to Pluripotency and Directed Differentiation of Human Cells with Synthetic Modified mRNA", *Cell Stem Cell* 7, 618-630 (2010); and Mandal, P. K. & Rossi, D. J. "Reprogramming human fibroblasts to pluripotency using modified mRNA", *Nature Protocols* 8, 568-582 (2013).

However, transfection efficiency and viability using multiple distinct nucleic acids is often problematic and requires in all or almost all instances multiple steps during which cells need to be transferred or otherwise manipulated. As a consequence, currently known transfection methods often require significant time to generate iPS cells, and viability and/or yield is often much less than desired.

Therefore, there is a need for improved transfection devices and methods for delivery of cargo of various sizes, and especially large and/or multi-component cargo into a cell in a manner that will not or only minimally adversely affect the cell.

SUMMARY OF THE INVENTION

The inventive subject matter is directed to systems and methods for transfection devices in which a macrostructure, a complex macrostructure, or multiple different macrostructures are delivered under pressure from a deformable fluid reservoir to cells contained in a container. Most preferably, the deformable fluid reservoir is coupled to the container via a microporous membrane having a pore size suitable to deliver the macrostructure to the cell, which is thought to internalize the macrostructure via active endocytosis. Such devices are characterized by their high transfection efficiency, even with complex or multiple macrostructures, and low rate of cell damage.

In one aspect of the inventive subject matter, a method of changing genetic content of a cell that includes a step of providing a plurality of cells and exposing the cells to a transfection medium comprising a transfection reagent in association with a plurality of distinct nucleic acids. Most typically, the step of exposing the cells includes a step of applying pressure to the transfection medium to thereby force the transfection medium against the cells for a time and at a pressure effective to introduce the plurality of distinct nucleic acids into the cells. In a subsequent step, the cells are cultivated for a time sufficient to integrate or express the plurality of distinct nucleic acids. Additionally, it is contemplated that the steps of exposing and cultivating are performed in the same container containing the plurality of cells, typically for a time sufficient to allow for generation of clonal daughter cells. Therefore, extra manipulation steps on the cells are typically not required.

While not limiting to the inventive subject matter, it is generally preferred that the step of exposing the cells is non-ballistic and that the pressure to the transfection medium is at least 100 hPa. Typically, the pressure to the transfection medium is maintained for a period of between 10 ms and 30 s, and the cells are retained in a fixed position (e.g., microfluidic channel or a cell adhesive layer) during the step of exposing and/or application of pressure.

In some contemplated aspects, the cells are typically located on a porous membrane during the step of exposing, and the transfection medium is forced through pores of the porous membrane. For example, the porous membrane may have an average pore density of between $1 \times 10^6$ pores/cm$^2$ and $1 \times 10^8$ pores/cm$^2$, and/or an average pore size of between 0.5 μm and 10 μm.

In other contemplated aspects, the change in genetic content reprograms a differentiation stage of a cell (e.g., from fully differentiated cell to induced pluripotent stem cell) or edits genomic information of a cell (e.g., via homology directed repair). With respect to the transfection medium it is contemplated that the medium comprises cationic liposomes, and/or that the plurality of nucleic acids comprise a guide RNA, a regulatory RNA (e.g., siRNA, miRNA, antisense RNA, etc.), and/or plurality of distinct RNAs that encode respective different proteins. Thus, the RNAs encode genes suitable for reprogramming a differentiated cell into a induced pluripotent stem cell (e.g., human cell). Alternatively, the plurality of nucleic acids may also comprise at least one DNA and at least one RNA, most typically suitable for genome editing (e.g., Crispr/Cas).

Various objects, features, aspects and advantages of the inventive subject matter will become more apparent from the following detailed description of preferred embodiments, along with the accompanying drawing figures in which like numerals represent like components.

DETAILED DESCRIPTION

Figure 1A:
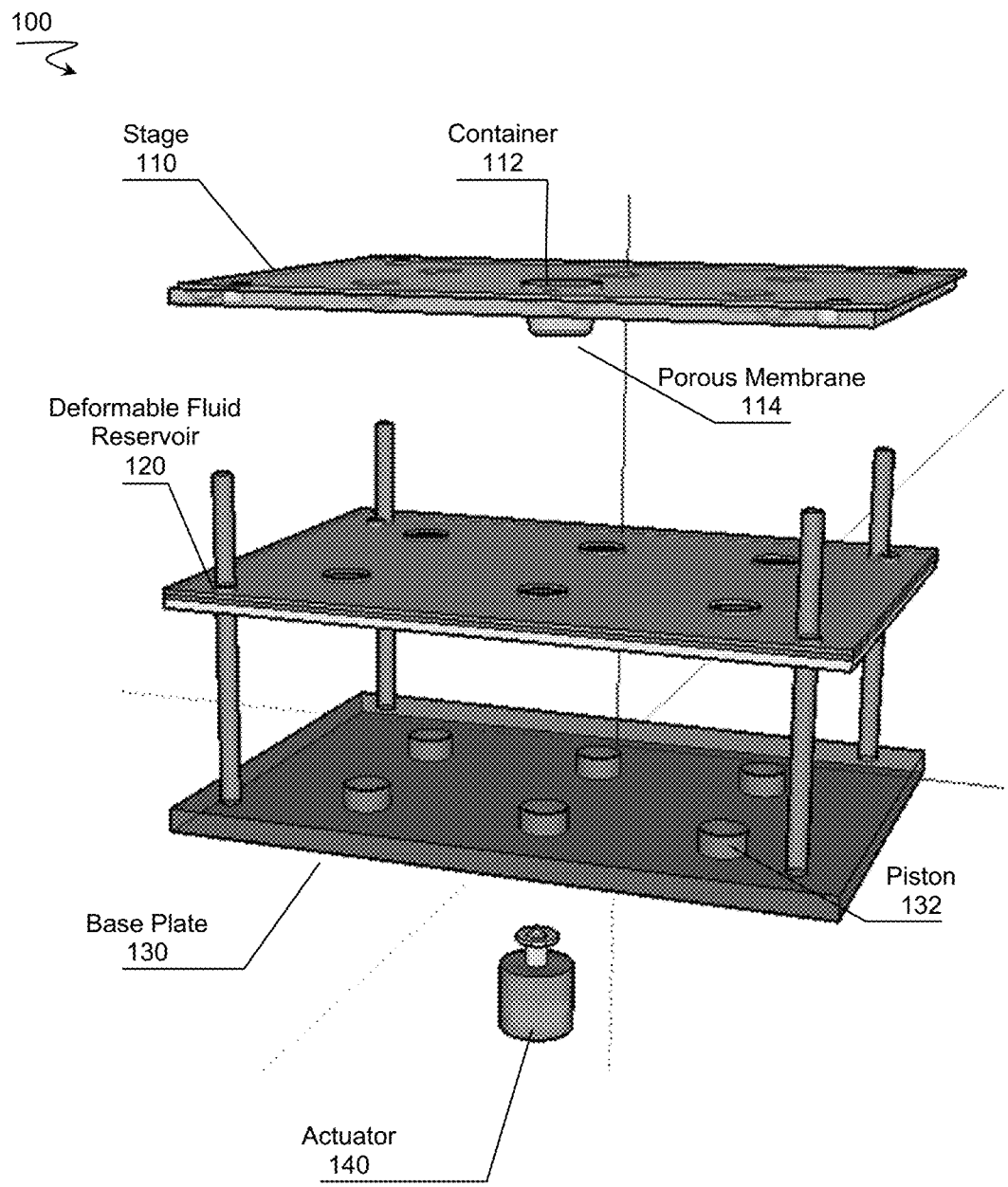
FIG. 1A is a schematic overview of one exemplary transfection device according to the inventive subject matter.

The inventors have discovered methods and devices to deliver various macrostructures, including cellular components (e.g., various and distinct nucleic acids, typically DNA and/or RNA in association with a transfection agent), cell organelles, and bacteria into a target cell in a non-disruptive manner. Moreover, contemplated methods and devices allow a large number of target cells to be modified, thus allowing for high-throughput transfection.

Most notably, the inventors have discovered that a relatively moderate mechanical force applied to macrostructures and target cells will lead to uptake of the macrostructures into the cells in a non-destructive manner, most likely via active endocytosis. Among other benefits, the inventors discovered that contemplated systems, methods, and devices are especially suitable for delivery of complex and diverse cargo, and particularly for gene editing and reprogramming of cells where multiple and relatively large nucleic acid molecules in complex or other association with transfection agents such as cationic liposomes are translocated into the cells.

Therefore, in one aspect of the inventive subject matter a transfection device for delivery of various macrostructures (e.g., mitochondria, bacteria, DNA/RNA lipoplexes, etc.) into target cells is contemplated in which an actuator provides a force that acts upon the macrostructures (typically in solution) and the cells such that the macrostructures that are proximal to the cells are taken up into the cells. In especially preferred transfection devices, movement of the cells is at least temporarily restrained (or adherent cells are employed), and the cells are initially separated from the macrostructures by a porous membrane, wherein the macrostructures are contained in a deformable fluid reservoir. Upon exertion of a force onto the deformable fluid reservoir, the macrostructures pass across the pores to the at least temporarily immobilized cells, triggering uptake of at least some of the macrostructures into the cells. It should thus be appreciated that the delivery of the macrostructures (e.g., transfection reagent in association with various and distinct nucleic acids) will not be a ballistic transfer in which a nucleic acid-loaded particle or droplet is shot at a sufficiently high velocity at a cell to ballistically penetrate the cell membrane. Instead, it is believed that the uptake is an active uptake process that is initiated or mediated by elevated pressure and/or enhanced local contact (e.g., active endocytosis).

For example, contemplated transfection devices will typically have a stage configured to receive and retain a container to which a deformable fluid reservoir is fluidly coupled. The stage is further configured to allow positioning of the container relative to the fluid reservoir such as to allow movement of macrostructures contained in a fluid from the deformable fluid reservoir into the container. In most preferred aspects, movement is facilitated via a porous membrane. The transfection device will also include an actuator that is operably coupled to the stage and that is configured to allow exertion of a force onto at least a portion of the deformable fluid reservoir in an amount effective to cause the movement of the macrostructure from the deformable fluid reservoir into the container. As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Figure 1B:
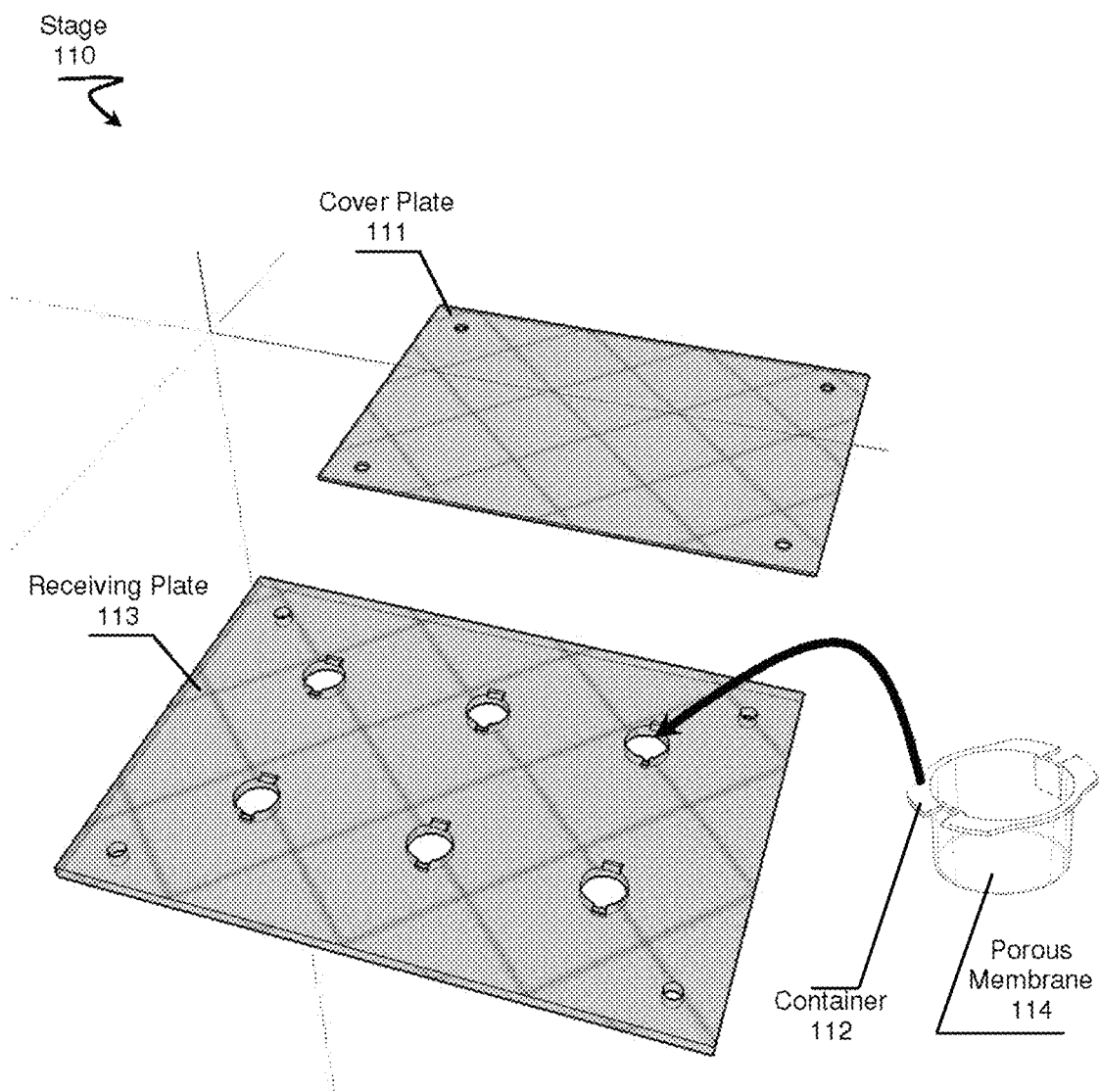
FIG. 1B provides a detail view of an exemplary stage and container of the device of FIG. 1A.

One exemplary device is schematically illustrated in the detail view of FIG. 1A. Here, the device 100 has a stage 110 that is configured to removably retain one or more containers 112 that contain cells for transfection in the example of FIG. 1A, the bottom surface of container 112 includes a porous membrane 114 and the lower portion of the container 112 is configured such as to sealingly engage with the a mating portion of the deformable fluid reservoir 120 as is shown in more detail below. Base plate 130 is disposed below the deformable fluid reservoir 120 and includes one or more pistons 132. Actuator 140 is disposed below base plate 130 and exerts an upwards force onto base plate 130 such that the pistons engage with a lower surface of the deformable fluid reservoir 120 as is also shown in more detail below. FIG. 1B provides a more detailed view of an exemplary stage 110. Here, the stage includes a receiving plate 113 having one or more openings to removably receive one or more containers 112 that have a porous membrane 114 at their lower surface. Container 112 is retained in the openings of the receiving plate via cover plate 111 such that when the actuator 140 exerts force upon the deformable fluid reservoir 120, the container remains in the same position relative to the stage.

Figure 1C:
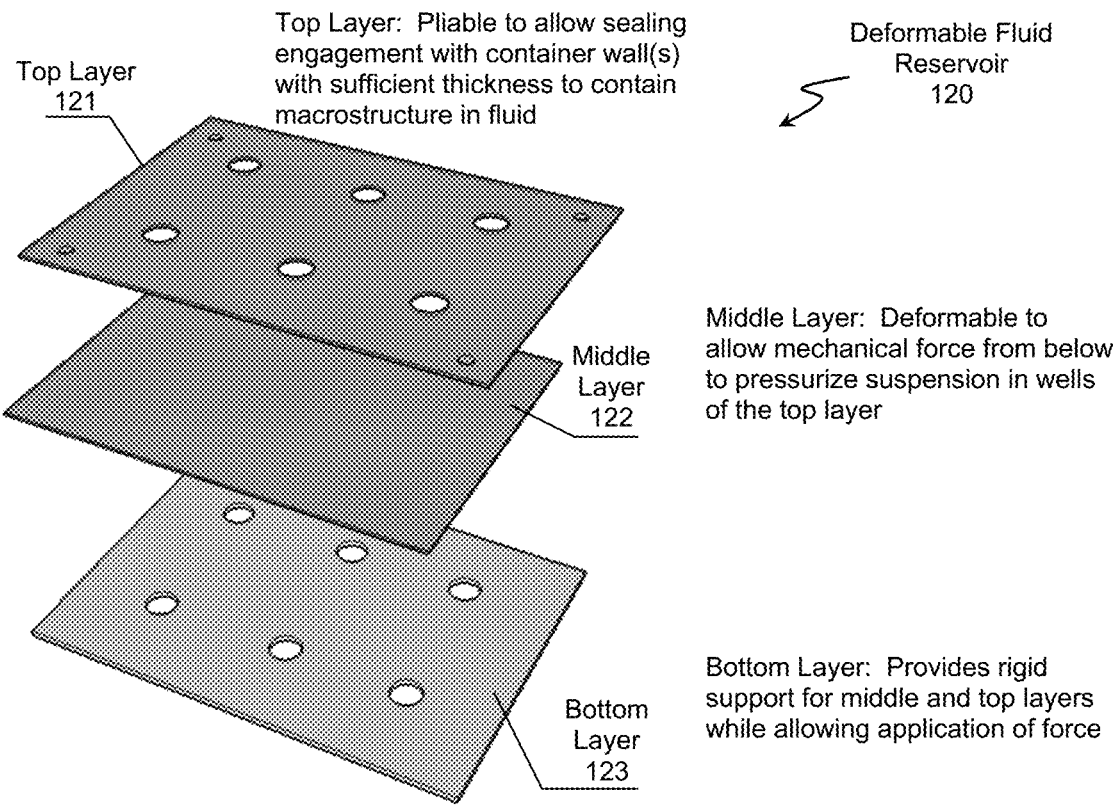
FIG. 1C provides a detail view of an exemplary deformable fluid reservoir (upper panel) and container engaged with the reservoir (lower panel) of the device of FIG. 1A.
Figure 1C:
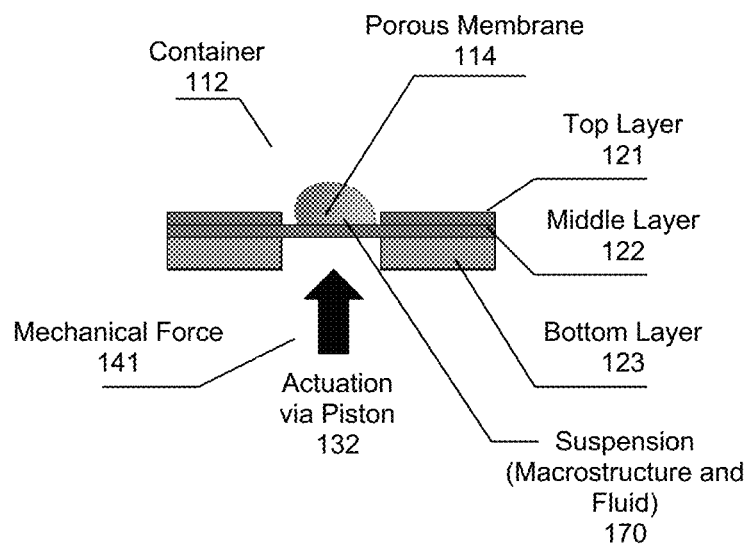

The upper panel of FIG. 1C shows a detail view of an exemplary deformable fluid reservoir 120 where the deformable fluid reservoir comprises multiple layers. Here, the top layer 121 comprises a pliable material that allows for sealing and retaining engagement with the container (see lower panel). While not limiting to the inventive subject matter, the top layer will have cutouts and have a thickness that is selected such as to provide sufficient volume for a fluid that contains the macrostructures when the container is sealingly engaged with the deformable fluid reservoir. Thus, it should be appreciated that the fluid that contains the macrostructures is contained by both, the deformable fluid reservoir and the porous membrane of the container. Middle layer 122 is typically made from a deformable material that together with the cutouts in the top layer forms a well for the liquid containing the macrostructures. In especially preferred aspects, the material for the middle layer is selected such as to allow a compressive force to act on the middle layer to thereby produce a fluid pressure of at least 50 hPa, or at least 100 hPa, or at least 200 hPa, or at least 400 hPa when the container is sealingly engaged with the container. The bottom layer 123 of the deformable fluid reservoir typically provides a rigid support platform for the middle and top layers and will typically include one or more openings for the actuator or piston 132 of the base plate 130.

The lower panel of FIG. 1C schematically illustrates a container 112 sealingly engaged (typically via press fit) with the top layer 121 such that the porous membrane 114 at the bottom of the container 112 is in fluid contact with the suspension 170 formed from the fluid and the macrostructures. Direct or indirect actuation (e.g., via piston 132) exerts mechanical force 141 onto the deformable middle layer 122. Middle layer and top layer are both supported by bottom layer 132. Thus, it should be appreciated that by providing a force onto the pliable middle layer, pressure in the fluid space defined by the middle layer, the top layer, and the porous membrane increases, leading to migration of the macrostructures through the pores across the porous membrane into the container and cells. In the example of FIG. 1C, the cells are retained at the bottom of the container (i.e., on the top side of the porous membrane, not shown) by a thin layer of CELL-TAK™ adhesive (polyphenolic proteins extracted from the marine mussel, *Mytilus edulis*, commercially available from Corning Inc., Bedford, Mass.).

Figure 2:
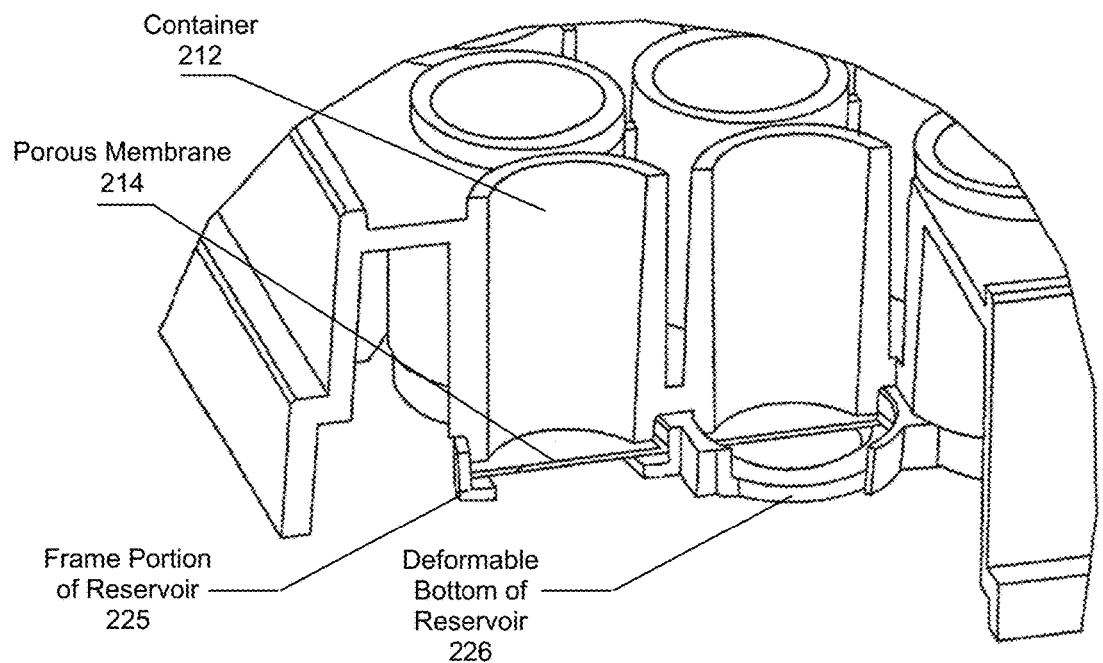
FIG. 2 illustrates another exemplary configuration of an assembly of the container and deformable fluid reservoir according to the inventive subject matter.

Another exemplary device is schematically shown in the detail view of FIG. 2 where the container 212 is configured as a well of a multi well plate. The deformable fluid reservoir in this device comprises a frame portion 225 that helps retain porous membrane 214. Also coupled to the frame portion 225 is a deformable bottom 226 of the reservoir. Thus, as noted previously, the porous membrane and a deformable portion of the fluid reservoir define the fluid reservoir that contains the macrostructure, and pressure onto the deformable portion will result in passage of the macrostructures through the pores of the porous membrane to the cells. Most typically, the fluid reservoir is preloaded, but it should be noted that the fluid reservoir may also include one or more fill and vent ports to fill the fluid reservoir before use.

With respect to suitable containers it is generally contemplated that the container may be made from a variety of materials, however, especially preferred materials are sterilizable by heat, radiation, and/or chemical treatment. Therefore, appropriate materials include various polymers (e.g., PE, PET, HDPE, PDMS, PC, etc.), glass, metals, and all reasonable combinations hereof. Regardless of the material, it is further preferred that the container has a shape suitable for receiving and retaining mammalian cells and that the container is configured to allow culturing of the cells. Thus, containers contemplated herein will typically have a volume between 0.1 mL and 250 mL, or even higher. For example, where the container is configured as a multi well plate, suitable volumes will be between 0.1 and 20 mL. On the other hand, where the container is configured as a culture flask or culture beaker, suitable volumes will be between 10 and 250 mL, or between 250 and 1000 mL. Thus, the shape of suitable containers is typically not limited and shaped considered suitable for use in conjunction with the teachings presented herein include cup shapes, cell culture flask shapes, box shapes, cylinder shapes, Petri dish shapes, etc. In still further contemplated aspects, containers will preferably be single use and disposable containers that are sterilized.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Regardless of the particular shape and volume, it is contemplated that the container will comprise (or be fluidly coupled to) at least one portion of a surface that includes the porous membrane. In most cases, the porous membrane forms at least a portion of a bottom surface of the container. There are numerous porous membrane known in the art, and all porous membranes are deemed suitable so long as such porous membranes are able to support and/or retain cells during transfection. For example, contemplated porous membranes may be made from various materials, including nylon, polytetrafluoroethylene (PTFE), expanded polytetrafluoroethylene (ePTFE), polyetheretherketone (PEEK), expanded polyetheretherketone (ePEEK), polyethylene (PE), polypropylene (PP), polyvinylidene fluoride (PVDF), ethyl vinyl acetate (EVA), thermoplastic polyurethane (TPU), or polyethersulfone (PES). In further contemplated aspects, the membrane will typically be relatively thin and may therefore have a thickness of between 1 μm and 1 mm, or between 3 μm and 0.5 mm, or between 5 μm and 250 μm. Viewed form a different perspective, suitable membranes will generally have a thickness of at least 1 μm, or at least 3 μm, or at least 5 μm, or at least 10 μm. It should be noted that the membrane thickness will also be determined at least in part by the pressure applied to the deformable fluid reservoir. However, support structures (e.g., support grid or mesh) to avoid membrane failure are also expressly contemplated herein.

The average pore size of the porous membrane will typically depend on various factors and the size and/or flexibility of the macrostructure will be particularly relevant. Therefore, it is contemplated that the average or median pore size of the porous membrane ranges from about 50 nm, or from about 100 nm, or from about 200 nm, or from about 300 nm, or from about 400 nm, or from about 500 nm, or from about 600 nm, or from about 700 nm, or from about 800 nm, or from about 900 nm, or from about 1 μm up to about 30 μm, or up to about 20 μm, or up to about 15 μm, or up to about 10 μm, or up to about 8 μm, or up to about 5 μm. In certain embodiments the median or average pore size in the porous membrane is about 1 μm or about 3 μm, or about 5 μm or about 10 μm, or about 15 μm. The term 'about', when used in conjunction with a numeral refers to a range spanning +/−10%, inclusive, around that numeral. For example, the term 'about 10 μm refers to a range of 9 to 11 μm, inclusive.

With respect to the pore density of the membrane it is contemplated that the density will be sufficiently high such that on average a cell will cover (or be located above) at least one pore, or at least two pores, or at least 3 pores, or at least 4 pores, or at least 5 pores, or at least 10 pores. Thus, the pore density in some embodiments will be between about $1\times10^5$ pores/cm$^2$ to about $1\times10^7$ pores/cm$^2$, or between about $5\times10^5$ pores/cm$^2$ to about $5\times10^6$ pores/cm$^2$, or at least $1\times10^5$ pores/cm$^2$, or at least $1\times10^6$ pores/cm$^2$, or at least $1\times10^7$ pores/cm$^2$. Viewed from a different perspective, the porous membrane comprises in some embodiments about a 1-10 μm diameter average pore size at about $1\times10^6$-$10^7$ pores/cm$^2$.

In still further contemplated aspects of the inventive subject matter, additional elements may be included with the container and membrane to at least temporarily retain cells in a fixed position on the porous membrane. For example, additional elements may include microfluidic channels though which the cells may be fed to/maintained on the membrane, a mesh to retain the cells on the membrane, or the membrane may be coated with an adhesive that temporarily retains the cells on the membrane. There are various adhesives known in the art, and all of them are deemed suitable for use herein, including collagen matrices, CELL-TAK™ adhesive, poly-L-lysine, extracellular matrix proteins (e.g., collagen, fibronectin, laminin, etc.), or other adherents. Alternatively, it is noted that where adherent cells are used, no additional elements to retain the cells may be needed.

Deformable fluid reservoirs contemplated herein will generally have a volume suitable for retaining sufficient macrostructures to transfect a desirable number of cells. Consequently, depending on the cell number, the transfection efficiency, surface area of the porous membrane, and other factors, the volume of the deformable fluid reservoir may vary considerably. However, it is generally contemplated that the volume will be between about 10 μL and 5 ml (in some cases even higher), or between about 100 μL and 1 mL, or between about 50 μL and 500 μL, or between about 100

µL and 1000 µL. Similarly, the shape of the deformable fluid reservoir may vary considerably but it is generally contemplated that the particular shape will be at least in part determined by the shape of the container and the size of the porous membrane. Consequently, it is contemplated that the deformable portion will preferably a wall or wall portion, which may be homogenously deformed or locally, or that the deformable portion is replaced by a movable wall or wall portion (e.g., configured as a plunger). Alternatively, the entire deformable fluid reservoir may also be compressible. Moreover, it is contemplated that the deformable fluid reservoir will sealingly engage with the container such that the macrostructures will be able to flow from the reservoir (typically within the fluid) into the container and to the cells on the porous membrane. In especially preferred aspects, sealing engagement of the deformable fluid reservoir with the container is maintained at pressures in the deformable fluid reservoir of at least 50 hPa, at least 100 hPa, at least 200 hPa, at least 400 hPa, at least 800 hPa. Viewed from a different perspective, the sealing engagement may be maintained at pressures between 1 and 1000 hPa, between 10 and 800 hPa, between 50 and 600 hPa, or between 100 and 1000 hPa.

In still further contemplated aspects of the inventive subject matter, the deformable fluid reservoir may be coupled to or include or one or more ports through which a fluid containing the macrostructures can be introduced, preferably using sterile techniques and sterile adapters (e.g., Luer lock adapters). Where desirable, vent and/or discharge ports may be included to facilitate loading and unloading of the deformable fluid reservoir. Most typically, the deformable fluid reservoir will be removable. However, permanently affixed deformable fluid reservoirs are also contemplated (in such case, the reservoirs may be prefilled with a fluid and macrostructures).

Among other things, macrostructures suitable for use herein will include cell organelles (e.g., nucleus, mitochondria, chloroplast, ribosomes, etc.), viruses and microorganisms (e.g., gram$^+$ and gram$^-$ bacteria, etc.), various macromolecules, and especially recombinant and natural nucleic acids alone or in combination with a transfection agent (e.g., native, synthetic or artificial chromosomes, miRNA, siRNA, plasmids, double minute chromosomes, etc.), proteins and/or protein complexes, and drug delivery particles.

Therefore, the type of fluids appropriate for storage and movement may vary considerably, but it is generally preferred that the fluids include physiologically acceptable solutions (e.g., isotonic and buffered solutions), growth media, etc. Examples of suitable fluids include experimental buffer, PBS, DMEM, HBSS, Opti-MEM, DMEM without Ca2+, or other media amenable to the nature of cargo material. The macrostructures in the fluid can also comprise one or more lipid carriers. Example lipid carries can Lipofectamine, Transfectace, Transfectam, Cytofectin, DMRIE, DLRIE, GAP-DLRIE, DOTAP, DOPE, DMEAP, DODMP, DOPC, DDAB, DOSPA, EDLPC, EDMPC, DPH, TMADPH, CTAB, lysyl-PE, DC-Cho, -alanyl cholesterol; DCGS, DPPES, DCPE, DMAP, DMPE, DOGS, DOHME, DPEPC, Pluronic, Tween, BRIJ, plasmalogen, phosphatidylethanolamine, phosphatidylcholine, glycerol-3-ethylphosphatidylcholine, dimethyl ammonium propane, trimethyl ammonium propane, diethylammonium propane, triethylammonium propane, dimethyldioctadecylammonium bromide, a sphingolipid, sphingomyelin, a lysolipid, a glycolipid, a sulfatide, a glycosphingolipid, cholesterol, cholesterol ester, cholesterol salt, oil, N-succinyldioleoylphosphatidylethanolamine, 1,2-dioleoyl-sn-glycerol, 1,3-dipalmitoyl-2-succinylglycerol, 1,2-dipalmitoyl-sn-3-succinylglycerol, 1-hexadecyl-2-palmitoylglycerophosphatidylethanolamine, palmitoylhomocystiene, N,N'-Bis (dodecyaminocarbonylmethylene)-N,N'-bis((-N,N,N-trimethylammoniumethyl-aminocarbonylmethylene) ethylenediamine tetraiodide; N,N'''-Bis (hexadecylaminocarbonylmethylene)-N,N', N'''-tris((-N,N,N-trimethylammonium-ethylaminocarbonylmethylenediethylenetriamine hexaiodide; N,N'-Bis(dodecylaminocarbonylmethylene)-N,N''-bis((-N,N,N-trimethylammoniumethylaminocarbonylmethylene)cyclohexylene-1,4-diamine tetraiodide; 1,7,7-tetra-((-N,N,N,N-tetramethylammoniumethylamino-carbonylmethylene)-3-hexadecylaminocarbonyl-methylene-1,3,7-triaazaheptane heptaiodide; or N,N,N',N'-tetra((-N,N,N-trimethylammonium-ethylaminocarbonylmethylene)-N'-(1,2-dioleoylglycero-3-phosphoethanolaminocarbonylmethylene) diethylenetriamine tetraiodide.

Actuators include all devices capable of compressing the deformable fluid reservoir to an extent that the macrostructures will move through the pores to the cells. Thus, suitable actuators will include mechanical actuators (e.g., piston, screw drive, solenoid, etc.), hydraulic actuators (e.g., using aqueous fluid or oil), or pneumatic actuators (e.g., femtojet), even manual actuators. Therefore, it should also be appreciated that the actuator may be replaced by a pressurization device that directly pressurizes the contents of the deformable fluid reservoir, and suitable devices may include fluid pumps and pneumatic pumps. In still other aspects of the inventive subject matter, the compression is directly performed on the cells and may this include planar pressure elements, rollers, etc., or pressurized fluid droplets enclosing macrostructures may be accelerated onto the cells (e.g., via fluid jet devices, or inkjet print heads, etc.), typically at pressures of less than 1000 hPa.

In still further preferred aspects, the actuator operation is performed via a controller that is configured to move the actuator such that movement of the actuator effects deformation of the deformable fluid reservoir, and with that pressurizes the fluid. The inventors have discovered, as is shown in more detail below, that cell transfection is particularly effective in a relatively small range of conditions. In especially preferred aspects, the controller is configured to apply pressure via the actuator for a period of time ranging from about 10 ms to about 30 s, or from about 20 ms to about 15 s, or from about 20 ms to about 300 ms. Thus, the controller will typically operate the plunger such that the deformable fluid reservoir is pressurized for at least about 10 ms, at least 25 ms, at least 50 ms, at least 100 ms, or at least 500 ms, or at least 1 s, or at least 5 s, but in most cases less than 10 s, or less than 20 s, or less than 30 s, or less than 60 s. In some instances, pressurization may also last about 1 min, or up to about 1.5 min, or up to about 2 min, or up to about 2.5 min, or up to about 5 min. Most typically, however, the controller will be configured to effect pressurization for a period of time ranging from about 10 ms up to about 500 ms.

The controller is also preferably configured such as to effect pressurization of the fluid in the deformable fluid to a pressure of at least 10 hPa, at least 20 hPa, at least 50 hPa, at least 100 hPa, at least 200 hPa, at least 400 hPa, or at least 800 hPa. Therefore, suitable pressure ranges effected by the controller will be between 10 hPa and 1000 hPa, or between 20 hPa and 800 hPa, or between 40 hPa and 400 hPa, or between 50 hPa and 500 hPa. Additionally, it should be appreciated that the slope of pressure increase may vary considerably, and in most cases maximum pressure levels will be attained within less than 10 s, or less than 5 s, or less than 1 s, or less than 500 ns, or less than 250 ms. Of course, it should be recognized that the controller may also be programmable to a particular profile having a predetermined maximum pressure, predetermined pressure duration, and/or predetermined time to maximum pressure. Where feedback mechanisms are contemplated, it is typically preferred that the controller receives information of at least one pressure sensor in the device, typically located in the deformable fluid reservoir.

Figure 3:
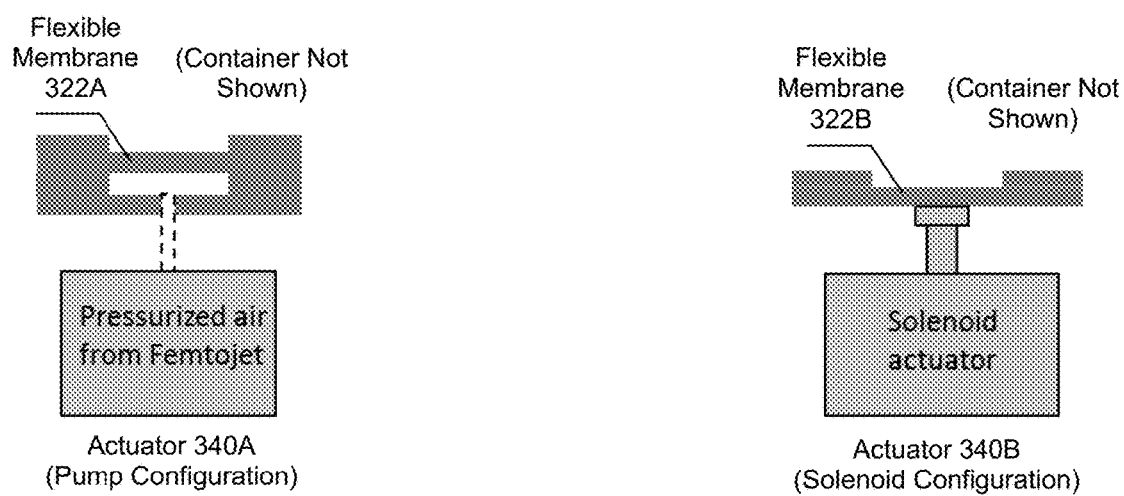
FIG. 3 illustrates an exemplary detail in which a pneumatic actuator (left panel) or a mechanical actuator (right panel) interacts with the deformable fluid reservoir.
Figure 4:
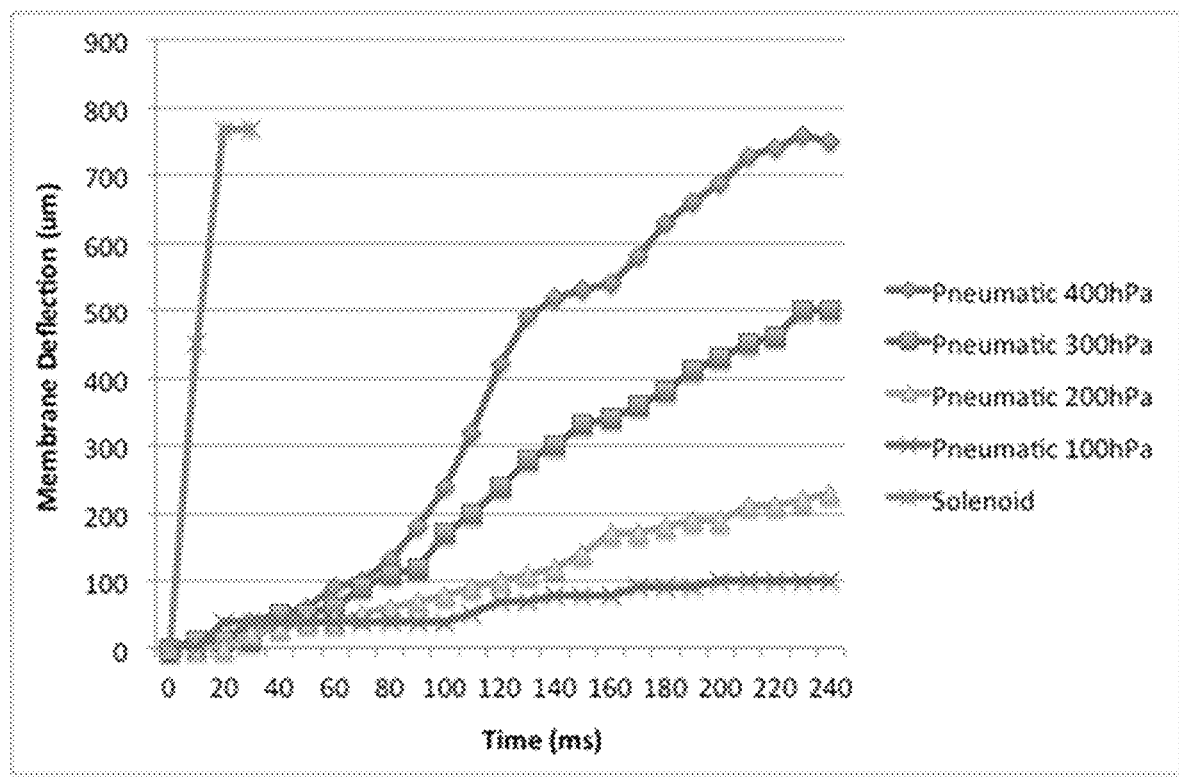
FIG. 4 is a graph illustrating exemplary deflection of a wall in the deformable fluid reservoir as a function of type and force applied to the wall.

FIG. 3 schematically and exemplarily illustrates two different modes of actuation as discussed above. On the left panel, the actuator 340A is a pneumatic actuator that provides pressurized air into the deformable fluid reservoir that has a flexible membrane 322A that forms part of the fluid reservoir above (container not shown). In such embodiment, the deformable portion is part of an inflatable chamber, the top of which forms the bottom of the fluid reservoir. Similarly, on the right panel, the actuator 340B is a solenoid actuator that directly presses against the deformable membrane 322B, the top of which forms the bottom of the fluid reservoir. As will be readily appreciated, the type of actuator and controller settings all fine-tuned pressure increases as can be taken from FIG. 4. Here, the graph depicts deflection kinetics of the deformable portion of the fluid chamber as a function of operation and type of actuator.

Experimental Data

The following experiments provide exemplary guidance on certain aspects of the device and methods of use, but should not be construed to be limiting in any manner. Unless specified otherwise, all transfection experiments were performed with a device according to FIG. 1A using the following typical experimental set-up:

Recipient cells are cultured or immobilized on top a 10 μm-thick polycarbonate porous membrane. For mitochondria delivery, membranes with 3 μm pore diameter and a density of $2 \times 10^6$ pores/cm$^2$ are used. For RNA and DNA lipoplex delivery, membranes with 1 μm pore diameter and $1.6 \times 10^6$ pores/cm$^2$ are used. Cargo suspension is loaded in a fluid reservoir made by stacking two layers of polydimethylsiloxane (PDMS). Bottom layer has a thickness of 0.5 mm and top layer has a thickness of 1 mm. Reservoir volume is 100 μL. The porous membrane is clamped and sealed onto the PDMS reservoir which connects the recipient cells with cargo suspension via its pores. A motorized actuator (solenoid actuator or stepper motor) is affixed to the bottom of the PDMS fluid reservoir. For delivery, the actuator is activated to deform the fluid reservoir and subsequently pump the cargo suspension into the recipient cells. For mitochondria delivery, a flow rate of 100 μL/0.02 sec is applied whereas for lipoplex delivery, a flow rate of 100 μL/10 sec is applied. After delivery, recipient cells can be cultured further on the porous membrane or re-plated onto other substrates for expansion or analyses. In the experiment demonstrating reprogramming human fibroblast into induced pluripotent cells, reagents and reprogramming protocol are described by P. Mandal and D. Rossi in *Nature Protocols* 8, 568-582 (2013). In the experiment demonstrating CRISPR genome editing, reagents and guide sequence construction are described by F. Ran et al. in *Nature Protocols* 8, 2281-2308 (2013).

Figure 5:
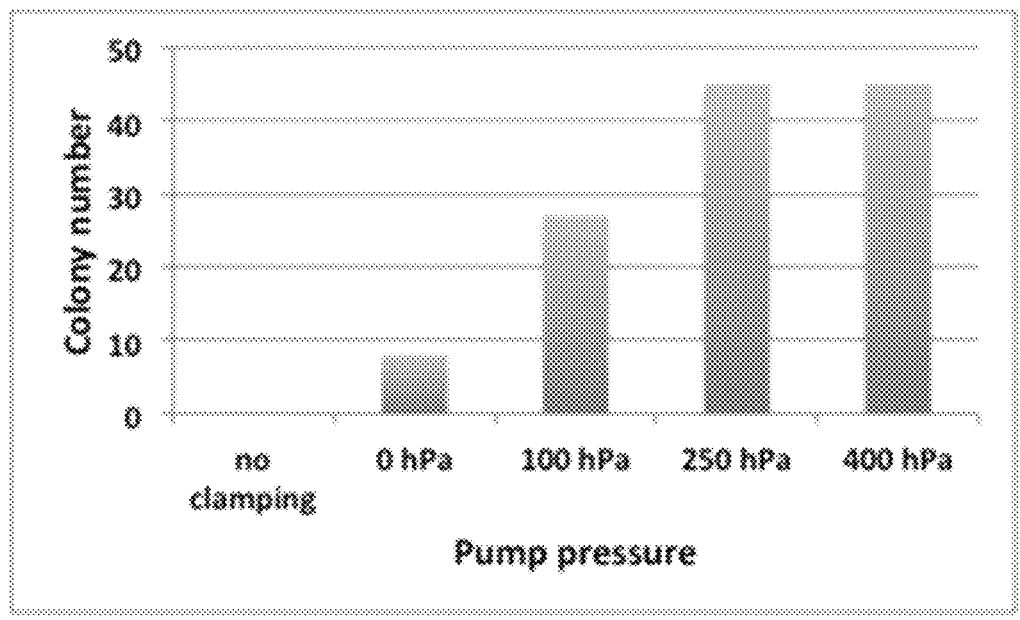
FIG. 5 is a graph depicting colony numbers as a function of pump pressure.
Figure 6:
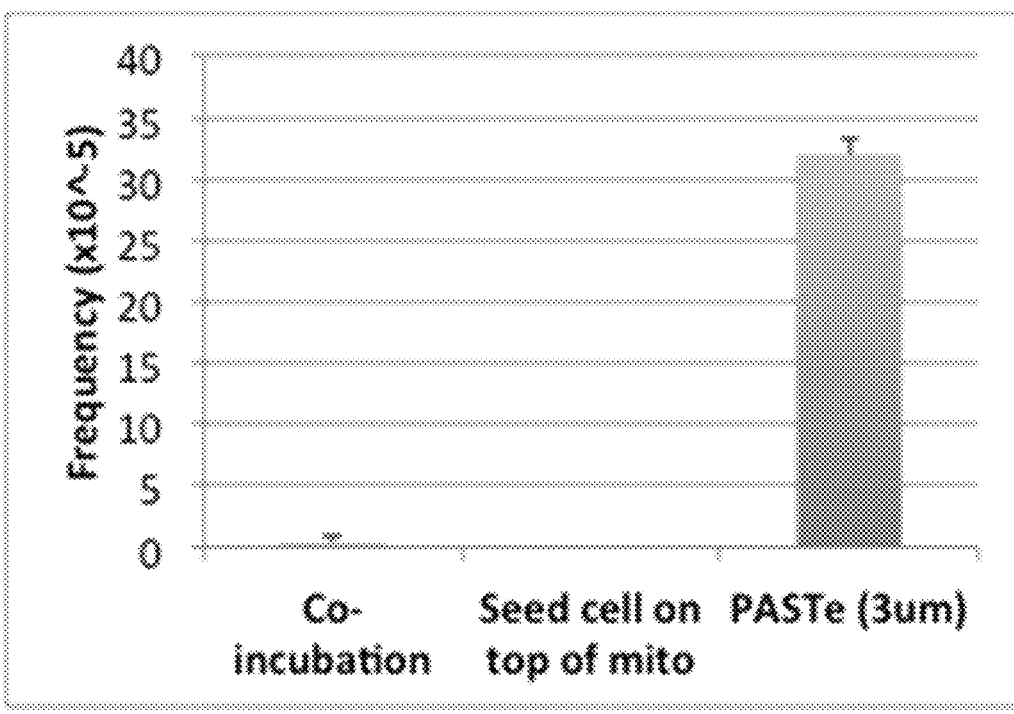
FIG. 6 is a graph depicting transfection frequency as a function of transfection method.

More specifically, FIG. 5 exemplarily illustrates suitable pump pressures to achieve transfection of mammalian cells with mitochondria, while FIG. 6 provides a comparison for transfection efficiency using the devices presented herein vis-à-vis conventional transfection methods. FIG. 5 presents graph that shows the number of successful mitochondria transfected colonies generated at various pressures. When the assembly is not clamped or locked down, no successful colonies were generated. Interestingly, at ambient pressure where the device is only under clamp pressure transfection occurs. Thus, it should be appreciated that the devices contemplated herein are able to achieve successful transfection at pressures that are at about ambient pressure, at least 50 hPa above ambient pressure, at least 100 hPa above ambient pressure, 200 hPa above ambient pressure, or even at least 400 hPa above ambient pressure. FIG. 6 illustrates a comparison of the transfection device contemplated herein with various other techniques. As can be readily seen from the graph, the device according to the inventive subject matter is capable of successfully transfecting cells with mitochondria as compared to other known techniques that failed to deliver mitochondria at any significant fraction. The data in FIG. 6 were generated using a PASTe (Pressure Assisted Cell Surgery Tool) device that has a porous substrate with 3 μm pores.

The colony forming frequency for mitochondria delivery (Fc) is calculated by dividing the number of transfected cells (Nt) that successfully grow colonies by number of initial cells (Ni); thus Fc=Nt/Ni. Interestingly, just after delivery, both the PASTe device and co-incubation delivered mitochondria with an efficiency of about 80%. However, only the PASTe device generated transfected cells capable of growing colonies that remained alive and inherited the transfected mitochondria.

Figure 7:
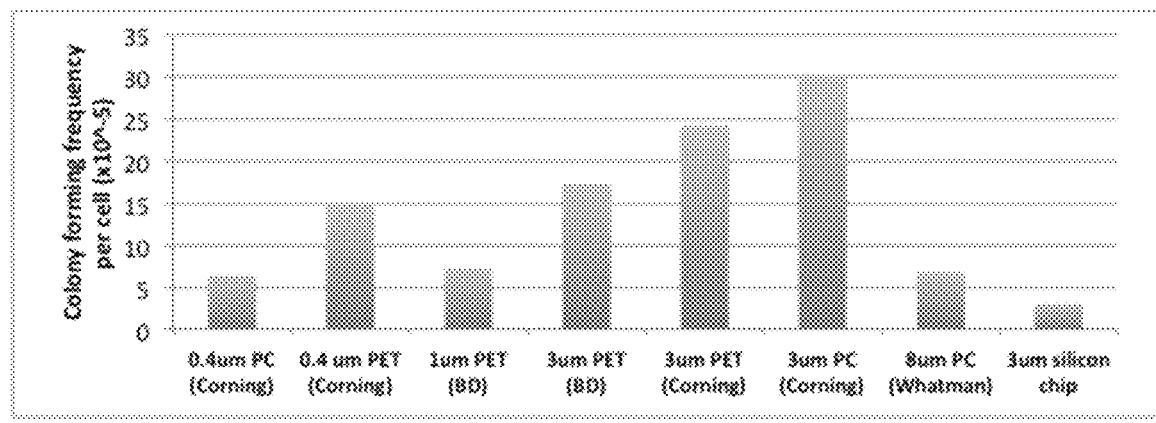
FIG. 7 is a graph depicting colony forming frequency after delivery of mitochondria as function of types of substrate and pore size.

FIG. 7 shows exemplary results for various porous materials that can be used with the devices according to the inventive subject matter. As can be readily seen from the graph, a broad spectrum of porous substrates including at least PC, PET, deformable membranes, or even rigid substrates such as silicon can be successfully employed. These substrates are readily available from manufactures including CORNING®, BECTON DICKENSON®, and WHATMAN®. Furthermore, the graph also indicates that transfection with mitochondria is successful with a range pore sizes from 0.4 μm through at least 8 μm. Most notably, the data also indicate that mitochondria delivery via contemplated transfection devices can have a success frequency that is at least $1 \times 10^{-5}$, more preferably at least $8 \times 10^{-5}$, even more preferably at least $1 \times 10^{-4}$, or yet more preferably at least $4 \times 10^{-4}$. Liposome delivery has successfully achieved efficiencies of at least 15%, including at least 70%.

Figure 8:
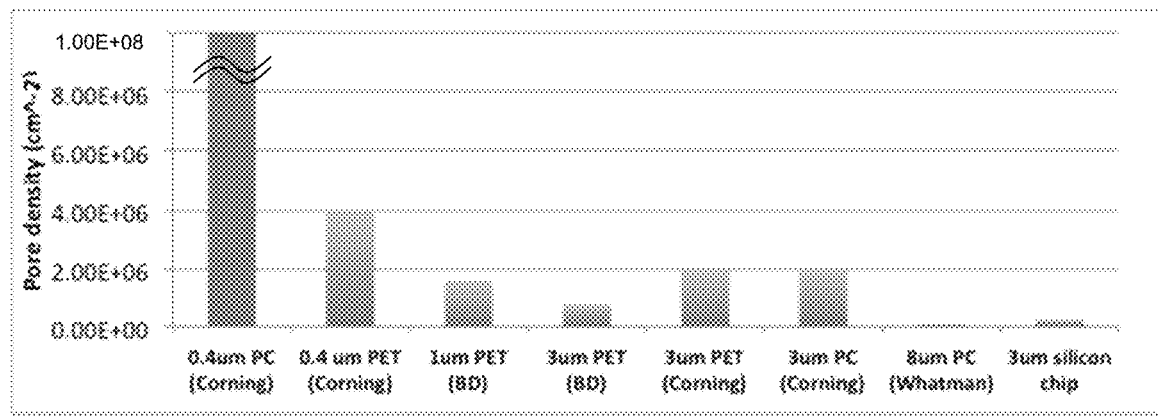
FIG. 8 is a graph depicting colony forming frequency after delivery of mitochondria as function of pore density.
Figure 9:
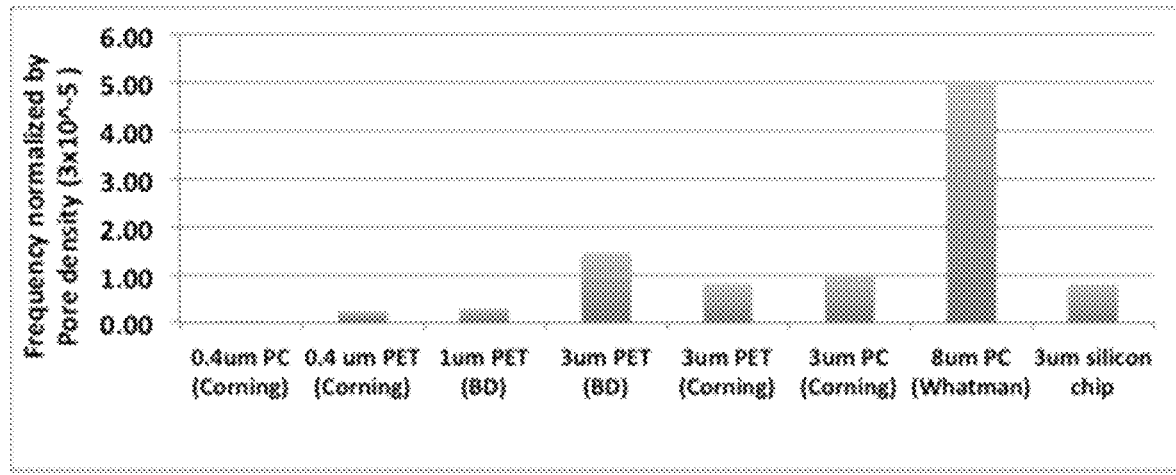
FIG. 9 is a graph depicting pore density-normalized colony numbers as a function of membrane materials and pore size.

FIG. 8 presents data using pore density for the substrates from FIG. 7. As can be readily taken from the data, acceptable pore densities (pores/cm$^2$) be a least $1 \times 10^4$ pores/cm$^2$, at least $1 \times 10^5$ pores/cm$^2$, at least $4 \times 10^6$ pores/cm$^2$, at least $1 \times 10^7$ pores/cm$^2$, or even at least $1 \times 10^8$ pores/cm$^2$. When the data from FIGS. 7 and 8 are combined an indication can be obtained which substrate will generate the most viable colonies as shown in FIG. 9 in which colony frequency has been normalized by pore density. At least with respect to mitochondria delivery and the set of substrates tested, an 8 μm pore size having relatively low pore density yields the most viable colonies at least for the experiments run.

Figure 10:
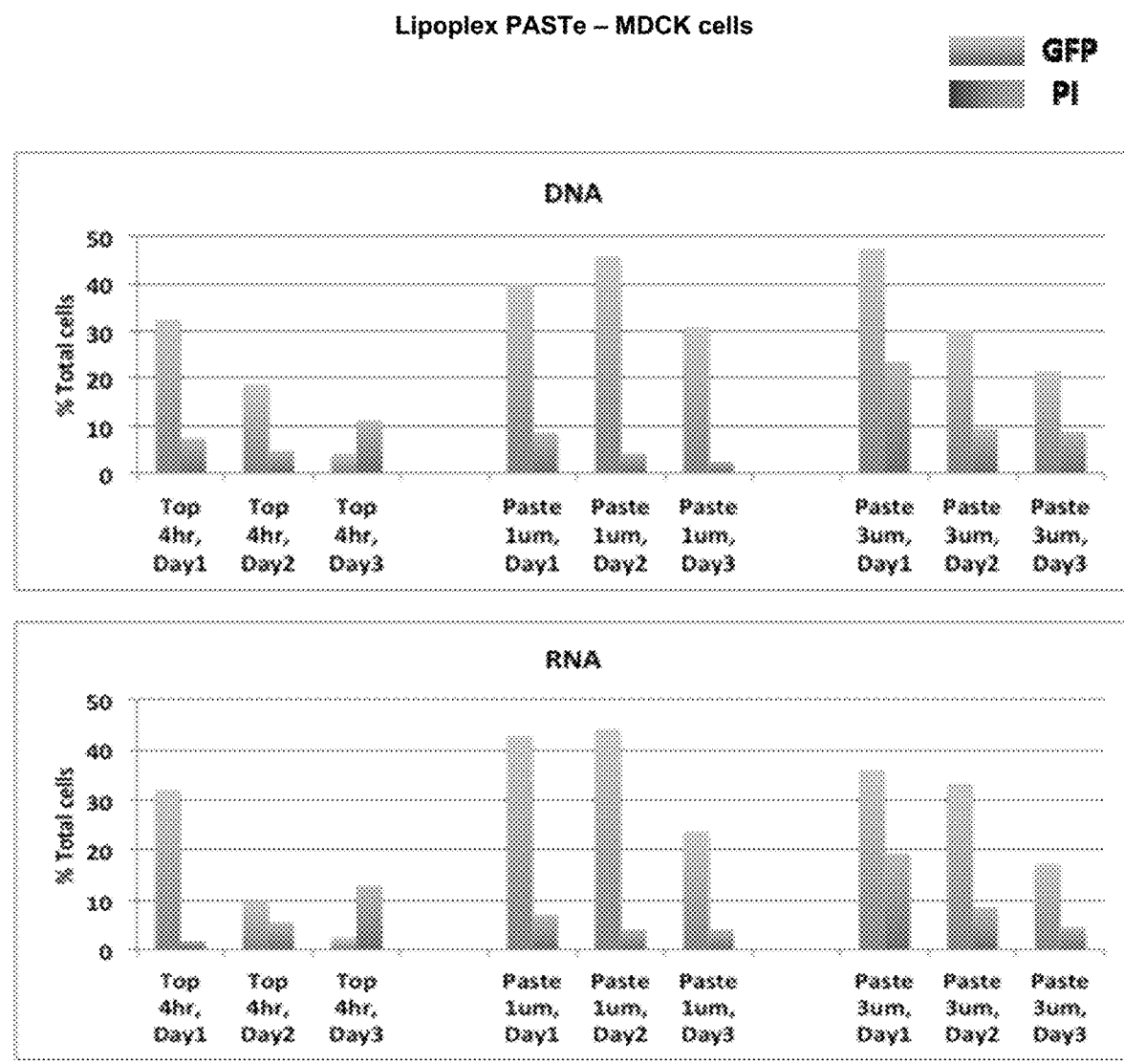
FIG. 10 is a graph depicting transfection rates for DNA (upper panel) and RNA (lower panel) using nucleic acid lipoplexes indicating success of transfection of DNA (upper panel) and RNA lipoplexes (lower panel) using contemplated methods relative to known top loading techniques.

FIG. 10 exemplarily shows results for transfection using DNA and RNA lipoplexes in conjunction with the devices contemplated herein as well as with traditional top transfection in which DNA and RNA lipoplexes were applied on top of MDCK cells. The delivered lipoplex contains green fluorescent protein (GFP) encoding DNA or RNA. As a result, successfully transfected cells are indicated by their GFP expression. As used herein, the term "lipoplex" refers to a composition that includes a nucleic acid (RNA or DNA) in association with a lipid, and most typically a cationic lipid that is in most cases organized as a micelle or liposome. Cell mortality after transfection is measured by propidium iodine (PI) staining. Percentage of PI positive cells represents the dead cell population. Cells were plated on day 0 and transfection was carried out on day 1, 2 and 3 respectively. PASTe yielded higher transfection rate than traditional applying lipoplex to top of the cells in all experiments, especially for higher cell densities (day 3). The PASTe approach (using a device as shown in FIG. 1) used a 1 μm pore substrate and a 3 μm pore substrate, and it is readily apparent that PASTe devices outperformed the traditional techniques.

The inventors further conducted experiments to investigate the influence of actuator speed on transfection efficiency. As can be seen from the Table below, transfection efficiency with mitochondria is a function of actuator speed.

| Pump method | pump speed (mm/s) | Cell density after delivery (per uL) | Colony # with delivered mtDNA |
| --- | --- | --- | --- |
| Solenoid | 100 | 39 | 252 |
| Pneumatic pump | 10 | 53.6 | 135 |
| Stepper motor | 2 | 86.3 | 29 |
| Stepper motor | 0.1 | 76.4 | 3 |

In contrast, the following table below indicates the results for DNA Lipoplex PASTe as a function of pumping speeds. Notably, however, where the transfection used nucleic acids, the transfection efficiency was not materially affected by actuator speed.

| Pump method | pump speed (mm/s) | GFP expression (%) | Median GFP intensity |
| --- | --- | --- | --- |
| Solenoid | 100 | 29.3 | 12,256 |
| Femtojet | 10 | 41.4 | 11,421 |
| Stepper | 1 | 39.6 | 11,944 |
| Top down transfection | — | 32.6 | 3,346 |

Figure 11A:
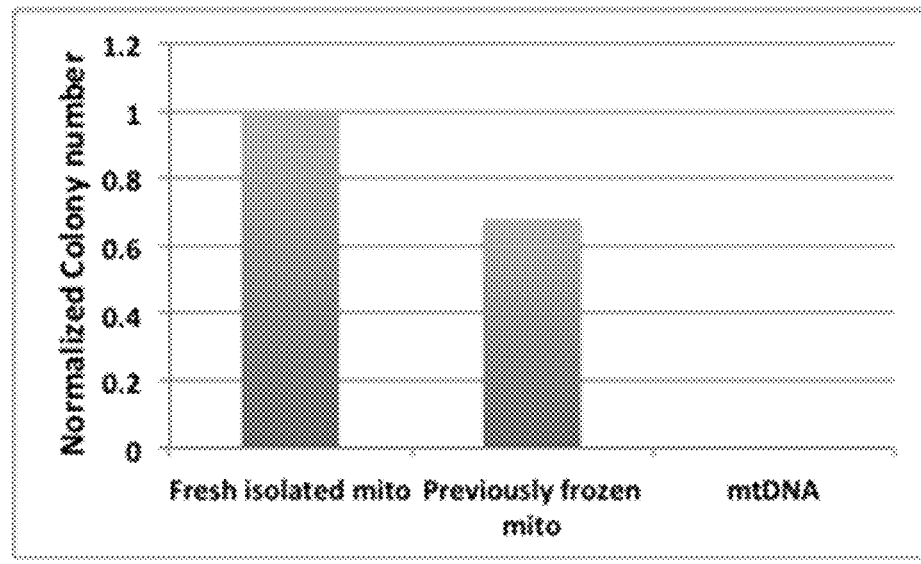
FIGS. 11A and 11B are graphs depicting colony numbers using contemplated devices and methods as a function of mitochondria material (upper panel) and mitochondria pretreatment (lower panel).
Figure 11B:
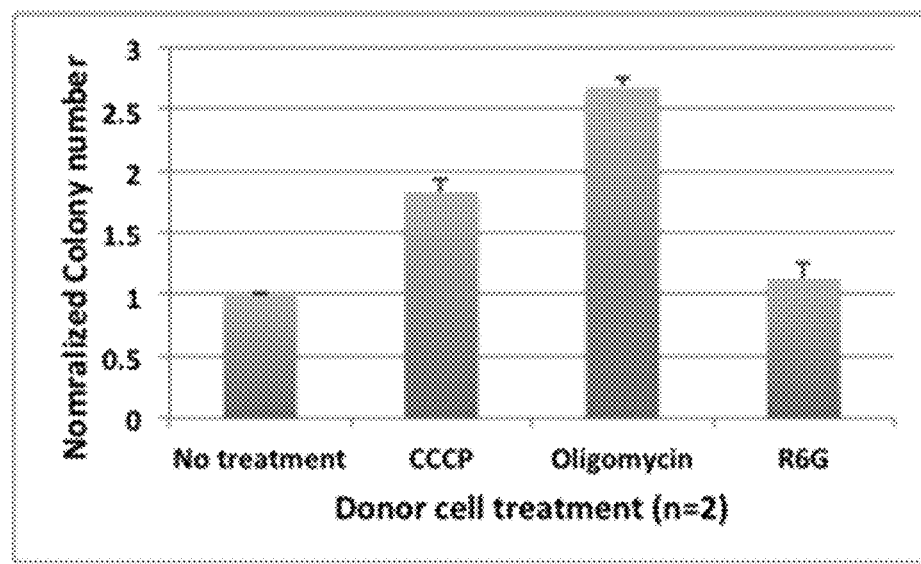

To further investigate the role of mitochondria status in cell transfection, the inventors compared fresh isolated mitochondria, previously frozen mitochondria, and mtDNA using the devices according to the inventive subject matter. Here, FIGS. 11A and 11B illustrate that the state of the isolated mitochondria is not critical for transfection results, nor that transfection efficiency is critically affected by various mitochondria inhibitors (CCCP: drug to dissipate mitochondrial membrane potential; Oligomycin: inhibits mitochondrial respiration; R6G: inhibits mitochondrial respiration).

Figure 12A:
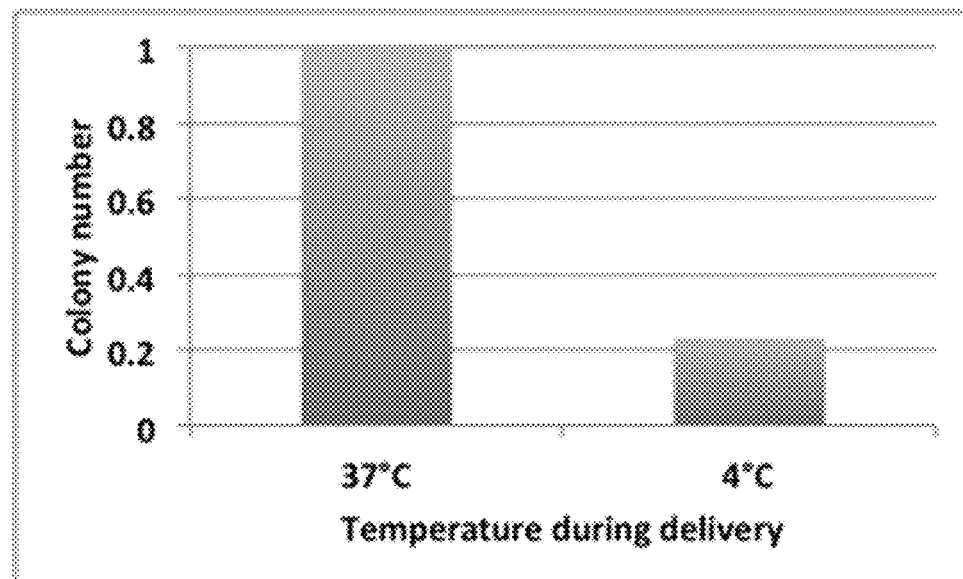
FIGS. 12A and 12B are graphs depicting transfection rates for delivery conditions (upper panel) and cell pretreatment (lower panel) using contemplated methods and devices.
Figure 12B:
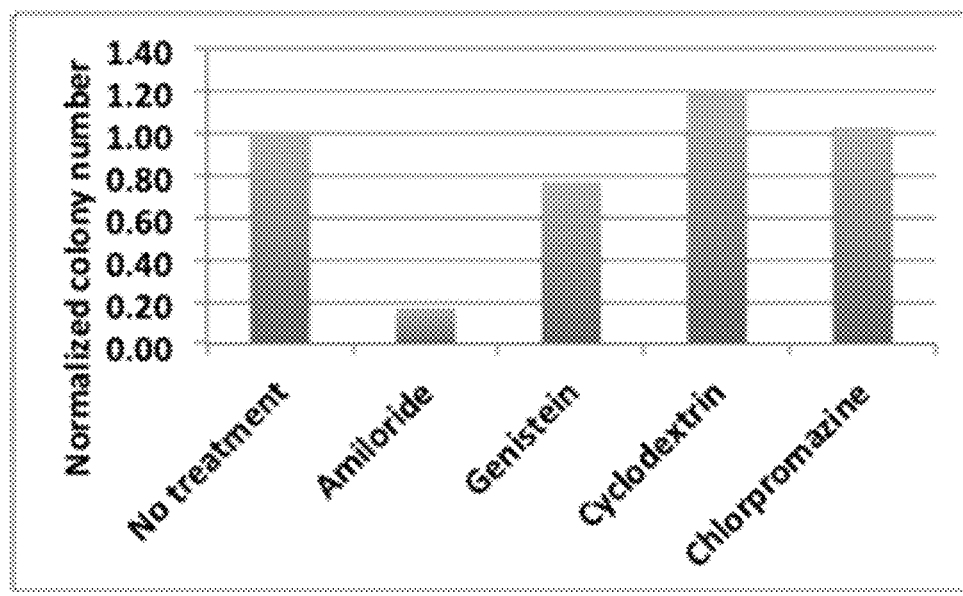

Further experiments, as exemplarily depicted in FIGS. 12A and 12B, suggest that the uptake of mitochondria is an active and energy dependent process. Here, transfection efficiency is significantly lower at lower temperatures. Amiloride is a macropinocytosis inhibitor, Genistein and Cyclodextrin are caveolae mediated endocytosis inhibitors, and Chlorpromazine is a clathrin mediated endocytosis inhibitor. As can be seen from these experiments, amiloride significantly inhibited colony formation and thus suggests an active update mechanism (e.g., via endocytosis, and especially macropinocytosis).

Figure 13A:
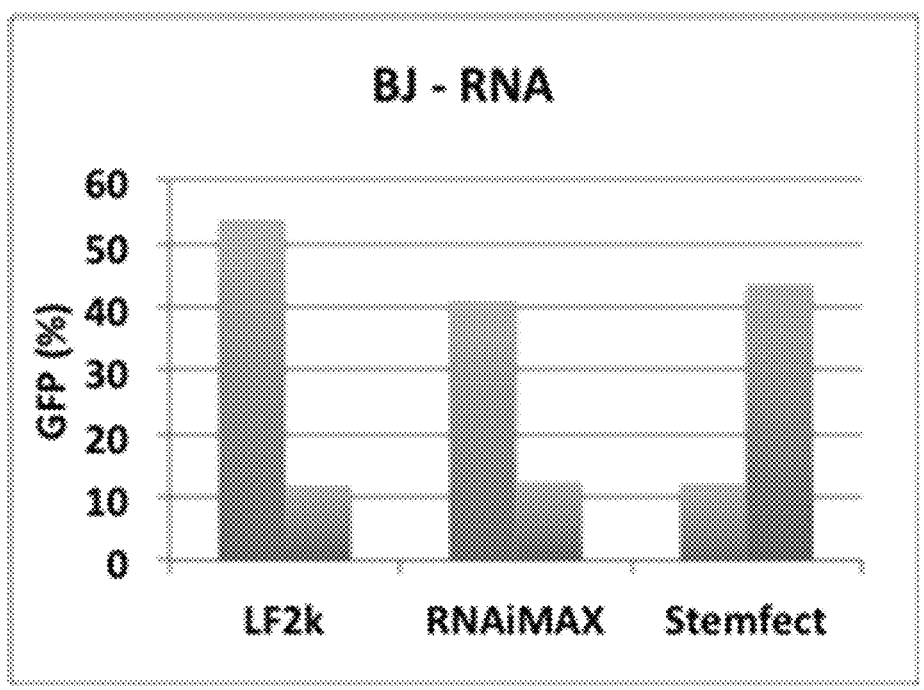
FIGS. 13A and 13B are graphs depicting transfection rates (upper panel) and GFP intensities (lower panel) as a function of transfection agents using contemplated methods and devices.
Figure 13B:
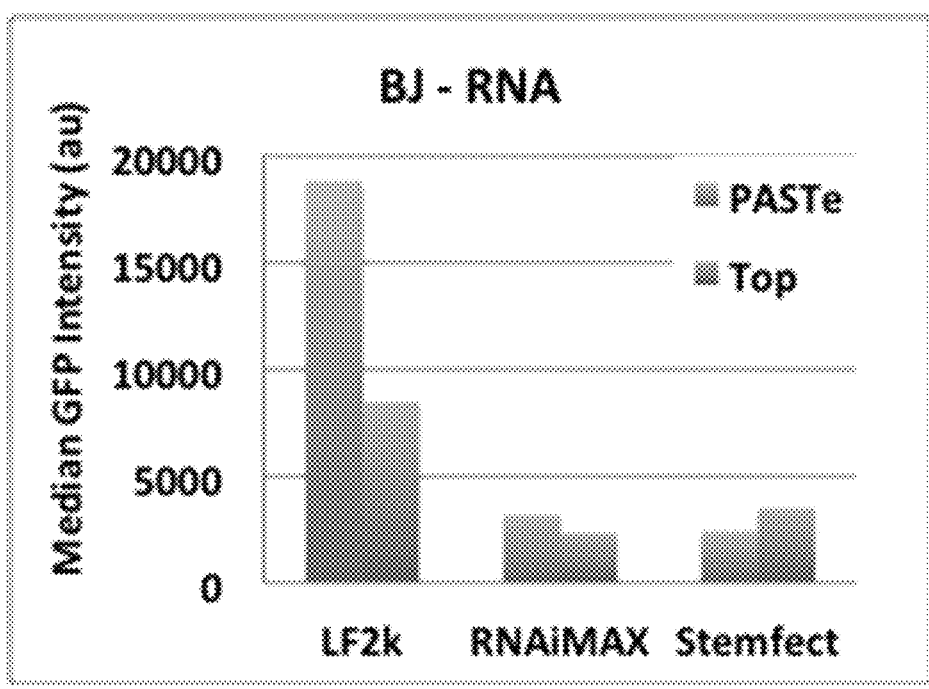

FIGS. 13A and 13B illustrate exemplary results from transfection of human skin fibroblasts comparing various transfection agents and methods for RNA. Here, GFP mRNA was complexed with various transfection reagents (Lipofectamine 2000, Lipofectamine RNAiMAX, and Stemfect) according to the manufacturer's protocols prior to delivery into the cells via top down transfection or PASTe. As is readily apparent not all transfection agents had the same effect, and the best agent tested was LF2k (Lipofectamine 2000) for PASTe devices, while stemfect was best for top transfection in terms of transfection efficiency as well as expression levels. Additionally, it should be appreciated that transfection efficiency as well as expression levels using PASTe were superior to conventional down transfection. Thus, cells can be effectively transformed using RNA to express recombinant protein at relatively high levels and transfection efficiency.

In yet another set of experiments, the inventors employed contemplated devices and methods to increase efficiency and reproducibility for reprogramming human fibroblasts into induced human pluripotent stem (iPS) cell. Here, mRNA cocktails containing reprogramming factors OCT4, KLF4, C-MYC, SOX2 and LIN28A were complexed with different transfection reagents according to manufacturer's protocol and delivered into human skin fibroblasts daily over a course of 2 weeks using top down transfection (P. K. Mandel and D. J. Rossi. Reprogramming human fibroblasts to pluripotency using modified mRNA. Nature Protocols 8, p. 568-582, 2013) and PASTe transfection. At the end of two weeks, successfully reprogrammed iPS colonies expressing pluripotent markers were counted and compared between different experimental conditions. As can be taken from the results in the table below, contemplated PASTe devices and methods were once more superior to traditional transfection using transfection agents without the device. Thus, treatment of cells with multiple distinct RNA species in association with transfection agents provided remarkably high transfection efficiency and expression levels (as can be taken from the FACS plots).

| PASTe | Well #1 LF2k | Well #2 RNAiMAX | Well #3 LF2k (ramp) | Well #4 LF2k + miRNA |
| --- | --- | --- | --- | --- |
| iPS colony # at D 14 | 29 | 21 | 23 | 73 |

| Top | Well #1 LF2k | Well #2 RNAiMAX | Well #3 Stemfect | Well #4 Stemfect + miRNA |
| --- | --- | --- | --- | --- |
| iPS colony # at D 14 | 0 | 3 | 0 | 0 |

Figure 14:
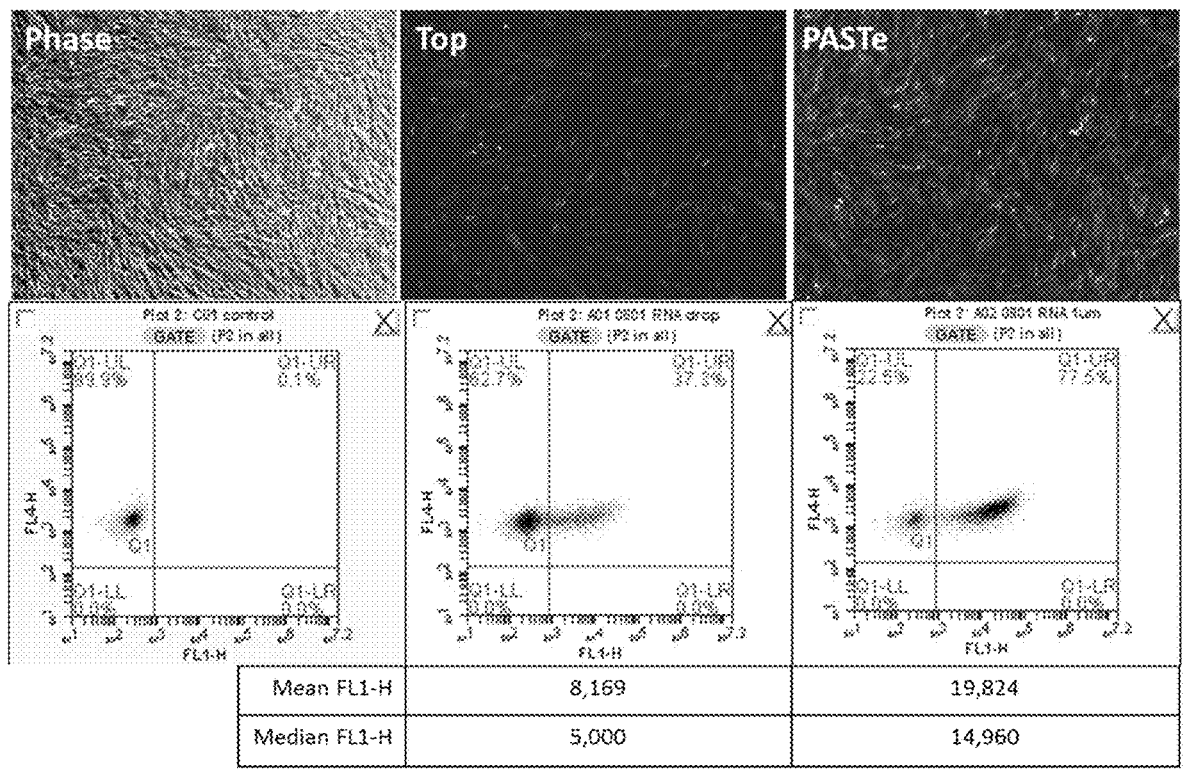
FIG. 14 illustrates results for control and comparative transfections (Top vs. PASTe) of BJ fibroblasts with RNA encoding GFP.

As can also be seen from the data, the mean reprogramming efficiency for PASTe is between 0.1-0.4%, while the mean reprogramming efficiency for Top transfection is about 0.015%. Likewise, the success rate for PASTe is 100%, while the success rate for Top down transfection is about 25%. Such benefits are unexpected as heretofore transfection agents alone were deemed critical to the success of the transfection and not the specific manner of delivery. FIG. 14 provides a comparison and contrast of a "Top" approach relative to the inventive PASTe approach for RNA transfection into BJ fibroblasts. Note that the PASTe approach not only provides for a significant number of transfection events relative to the Top approach, but also generates transfected cells that are highly differentiable from non-transfected cells (control group as shown in left panel). Thus, transfected cells can be selected based on FL1-H at a higher efficiency relative to transfected cells generated by the Top approach.

Figure 15:
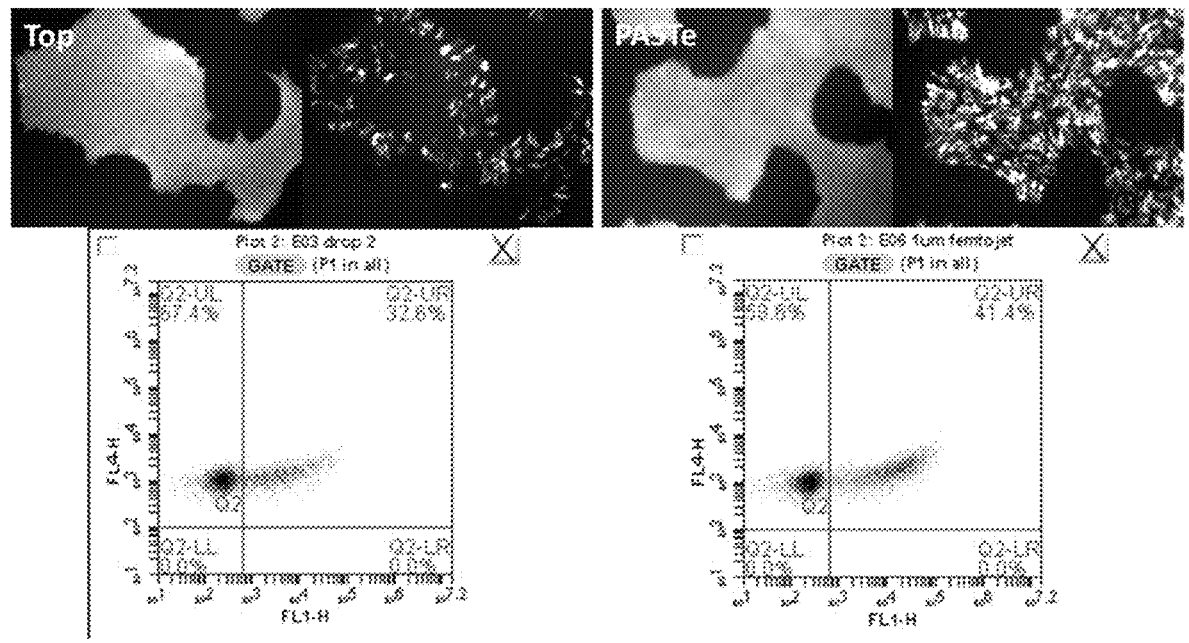
FIG. 15 illustrates results for control and comparative transfections (Top vs. PASTe) of H9 embryonic stem cells with RNA encoding GFP.

FIG. 15 provides an example where systems and methods according to the inventive subject matter were employed with H9 human embryonic stem cells (hESC). Here, the relative efficacy of a PASTe approach compared to a Top approach is shown for RNA transfection. Note that, as in FIG. 14, transfected hESC are more effectively differentiated from non-transfected cell based on FL1-H. Thus, systems and methods according to the inventive subject matter allow for a significantly more efficient mechanism for genomic manipulation and subsequent identification of transfected cells (e.g., reprogrammed cells, stem cells, etc.) than other known approaches.

Figure 16:
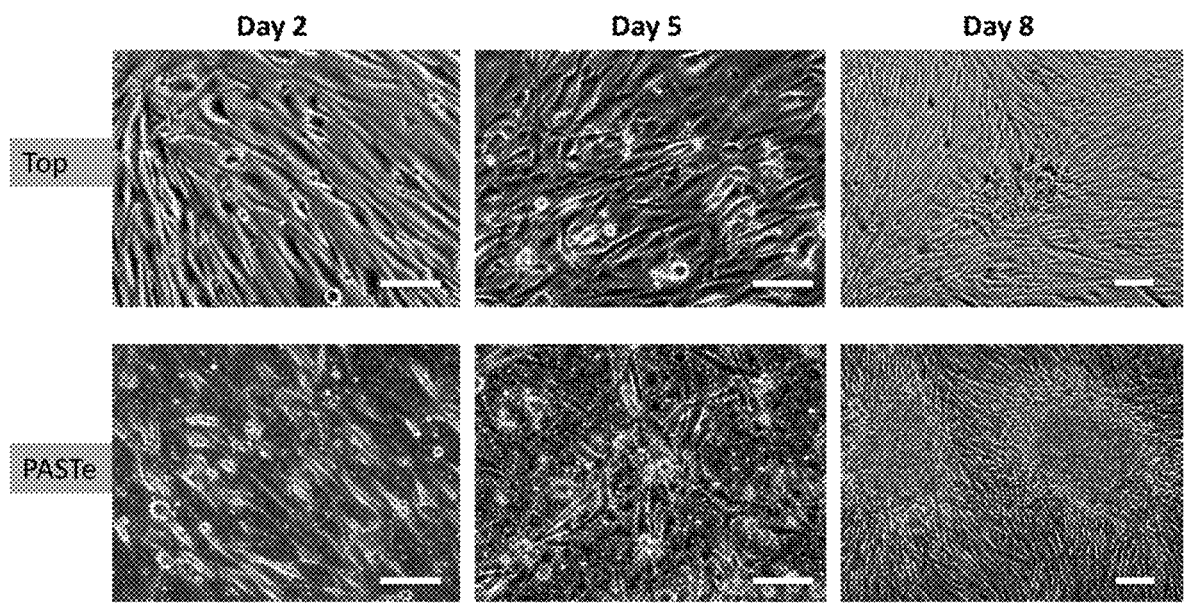
FIG. 16 illustrates time course results for comparative transfections (Top vs. PASTe) of BJ fibroblasts with RNA to reprogram the cells to form iPS.

As noted above with respect to FIG. 14, differentiated cells (e.g., skin fibroblasts) can be reprogrammed to induced pluripotent (IPS) cells by daily transfection of five transcription factors (OCT4, KLF4, C-MYC, SOX2, LIN28A) for a duration of approximately 14 days using heretofore known protocols. Unfortunately, such time frames can be unduly long. In order to determine the viability of PASTe with respect to time frames for genomic manipulation, the inventors followed the protocol described by P. Mandel and D. Rossi (*Nature Protocol* 8, 2013; see FIG. 1) and transfected BJ fibroblast cells with mRNA cocktails encoding KOMSL factors for 14 days. For comparison, mRNAs lipoplexes were delivered to BJ cells grown with irradiated feeder cells via the PASTe delivery approach as well as a conventional top transfection approach for comparison. As can be seen in FIG. 16, stem-cell-like colonies in PASTe transfected cells are produced as early as day 8. It should also be noted that by day 5, using the PASTe approach, stem-cell-like colonies already began to appear. The resulting PASTe colony sizes were larger and denser than those by Top transfection, and the morphology of the cells appeared to more closely resemble fully reprogrammed iPS cell colonies.

Interestingly, genome manipulation through PASTe RNA lipoplex transfection does not appear to depend on a pump speed (e.g., impulse generated), while PASTe mitochondrial transfer did appear to depend on pump speed as is shown in the tables below. The observed lipoplex transfection efficiency (e.g., GFP expression percentage) using the PASTe approach was relatively independent of pump speed. However, the PASTe mitochondria transfer and colony forming efficiency appeared to depend on pump speed. Thus, PASTe devices that are configured for genome manipulation via lipoplex-based transfection can adapt a pump method to fit a target circumstances (e.g., time, cost, latency, etc.).

PASTe Transfection (RNA lipplex) of hESC at different pump speed

| Pump Method | Pump Speed (mm/s) | GFP Expression | Mean GFP | Median GFP |
|---|---|---|---|---|
| Solenoid | 100 | 29.3 | 18,015 | 12,256 |
| Femtojet | 10 | 41.4 | 17,297 | 11,421 |
| Stepper | 1 | 39.6 | 17,182 | 11,944 |
| Top Transfection | | | | |
| –/– | –/– | 32.6 | 7,474 | 3,346 |

PASTe Transfection (Mitochondria) of 143btk rho(0) cells at different pump speed

| Pump Method | Pump Speed (mm/s) | Cell density/μL (after delivery) | Uptake (%) | Colony # |
|---|---|---|---|---|
| Solenoid | 100 | 39 | 12.4 | 252 |
| Femtojet | 10 | 53.6 | 61.3 | 135 |
| Stepper | 2 | 86.3 | 65.6 | 29 |
| Stepper | 0.1 | 76.4 | 61.6 | 3 |

Figure 17:
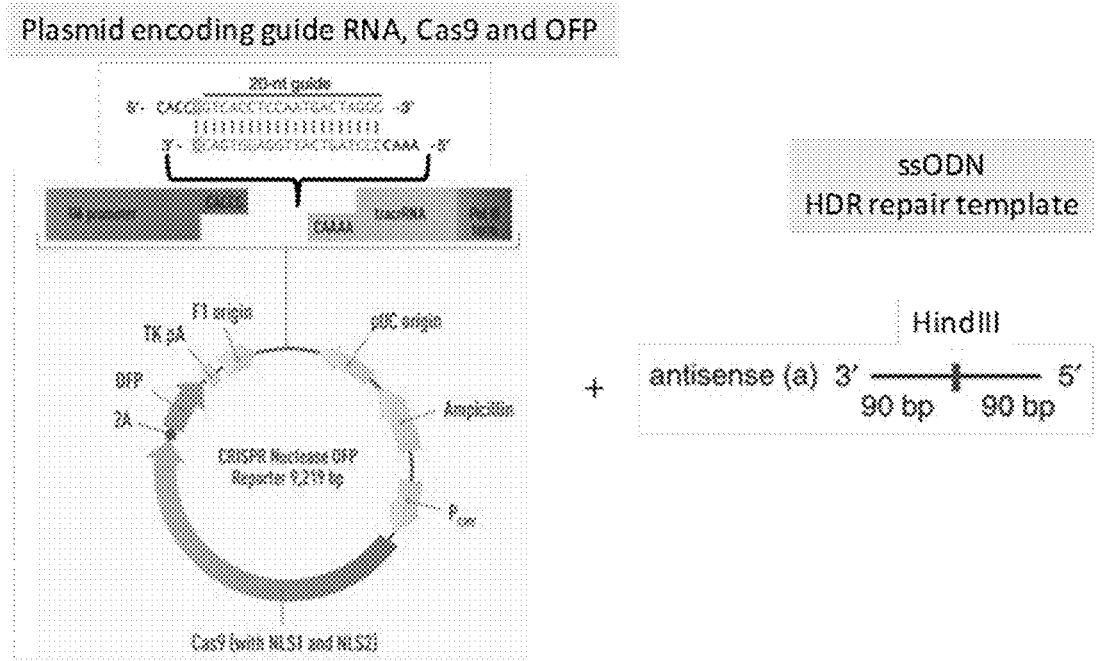
FIG. 17 is a schematic graph illustrating an exemplary approach for CRISPR gene editing using PASTe.
Figure 18:
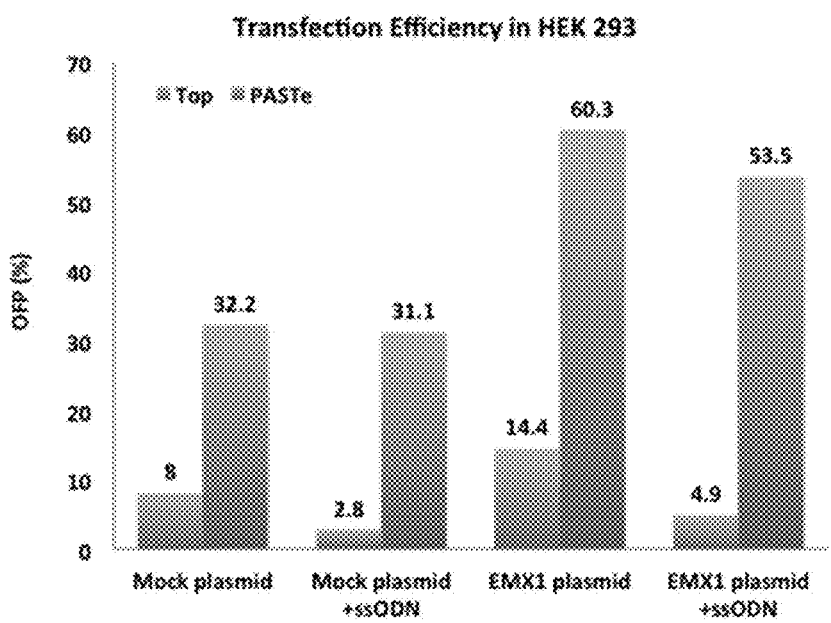
FIG. 18 is a graph depicting exemplary results for comparative transfections (Top vs. PASTe) of HEK 293 cells.
Figure 19:
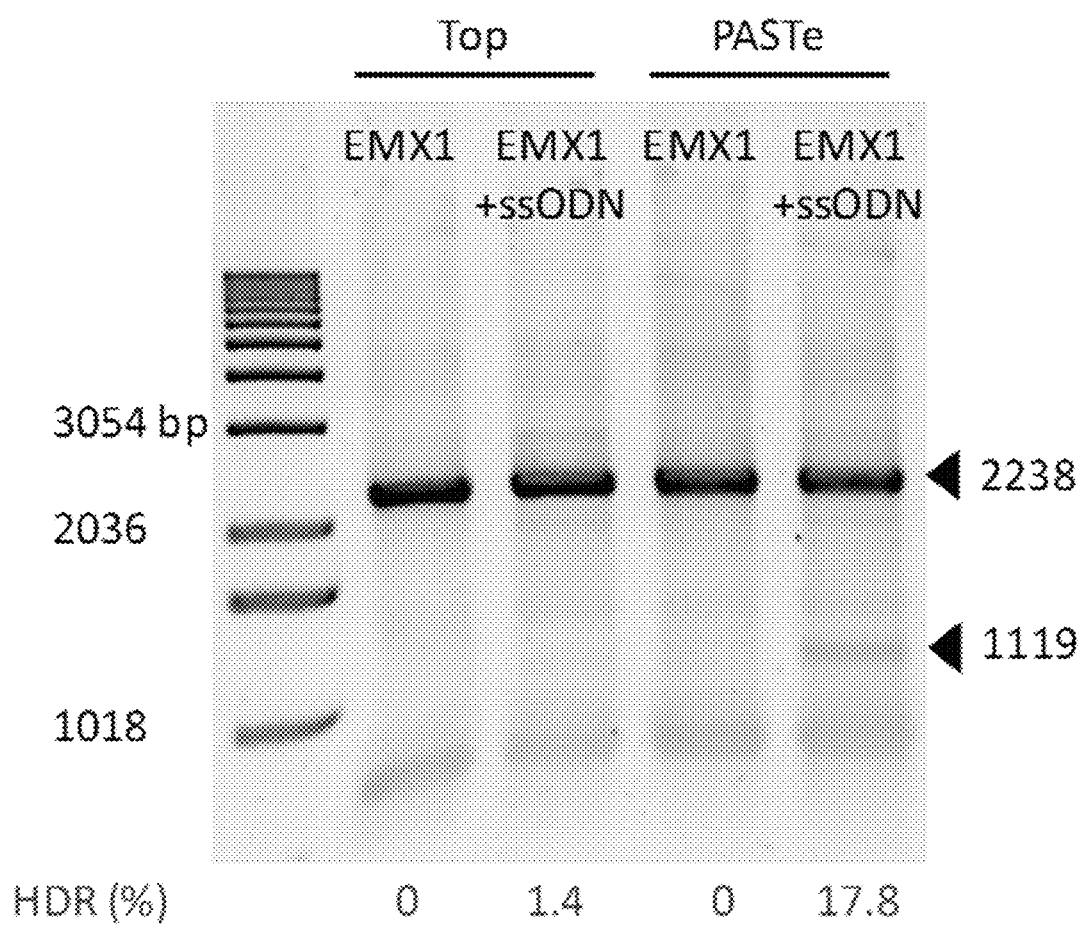
FIG. 19 is a photograph showing effects of gene editing efficiency by homology-directed repair (HDR) using EMX1.

Contemplated methods and devices can also be employed for transfection with complex cargo. For example, cells can be transfected with DNA and RNA in an approach to correct or change genomic information (e.g., via homology directed repair, genome editing via Crispr/Cas, etc.). As before, the different types of nucleic acids are preferably associated with respective transfection reagents prior to contacting the cells with the cargo. FIG. 17 schematically shows a PASTe-CRISPR genome editing approach in which the DNA portion comprises a plasmid that encodes the guide RNA, Cas9, and OFP, while the RNA portion includes single stranded nucleic acid HDR template. The components may be combined or separately be associated with the transfection agent (e.g., lipofectamine 2000) and were delivered into HEK293 cells using PASTe or Top down transfection. As before, PASTe transfection showed a significantly increased transfection efficiency as compared to Top down transfection and higher gene editing efficiency by homology directed repair. FIG. 18 provides exemplary results for transfection efficiency in HEK 293 cells, and FIG. 19 exemplarily demonstrates results for the gene editing efficiency by homology-directed repair (HDR).

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of changing genetic content of a cell in vitro, comprising:
    exposing a plurality of cells in vitro to a transfection medium comprising a transfection reagent and a plurality of nucleic acids, wherein the plurality of cells are located on a porous membrane,
    wherein exposing the cells comprises applying fluid pressure to the transfection medium from beneath the porous membrane to the cells to thereby force the transfection medium against the cells through the porous membrane for a time and at a pressure effective to introduce the plurality of nucleic acids into the cells by endocytosis.

2. The method of claim 1, wherein introduction of the plurality of nucleic acids into the plurality of cells is non-ballistic.

3. The method of claim 1, wherein the applied fluid pressure to the transfection medium is at least 50 kPa.

4. The method of claim 1, wherein the applied fluid pressure to the transfection medium is maintained for a period of between 10 ms and 500 ms.

5. The method of claim 1, wherein the plurality of cells are retained in a fixed position during exposing while applying fluid pressure.

6. The method of claim 5, wherein the plurality of cells are retained in a fixed position using a microfluidic channel or a mesh, or are attached to a cell adhesive layer.

7. The method of claim 6, wherein the cell adhesive layer comprises a cell adhesive moiety selected from the group consisting of a collagen matrix, a polyphenolic protein adhesive, a poly-L-lysine, and an extracellular matrix protein.

8. The method of claim 1, wherein the porous membrane is formed from a non-naturally occurring material.

9. The method of claim 8, wherein the non-naturally occurring material comprises a material selected from the group consisting of nylon, polytetrafluoroethylene (PTFE), expanded polytetrafluoroethylene (ePTFE), polyetheretherketone (PEEK), expanded polyetheretherketone (ePEEK), polyethylene (PE), polypropylene (PP), polyvinylidene fluoride (PVDF), ethyl vinyl acetate (EVA), thermoplastic polyurethane (TPU), and polyethersulfone (PES).

10. The method of claim 1, wherein the porous membrane has an average pore density of between $1 \times 10^5$ pores/cm$^2$ and $1 \times 10^7$ pores/cm$^2$.

11. The method of claim 1, wherein the porous membrane has an average pore size of between 50 nm and 30 µm.

12. The method of claim 1, wherein the porous membrane has a thickness between 1 µm and 1 mm.

13. The method of claim 1, wherein the plurality of nucleic acids comprise a guide RNA and a regulatory RNA.

14. The method of claim 1, wherein the plurality of nucleic acids comprise a multiplex of different guide RNA sequences.

15. The method of claim 1, wherein the plurality of nucleic acids comprise at least one DNA and at least one RNA.

16. The method of claim 15, wherein the at least one DNA comprises a plasmid that encodes a guide RNA, Cas9, or Orange Fluorescent Protein (OFP).

17. The method of claim 15, wherein the at least one RNA comprises a single stranded nucleic acid HDR template.

18. The method of claim 1, wherein the plurality of cells are stem cells or differentiated cells that are reprogrammed by transfection of a plurality of transcription factors.

19. The method of claim 1, wherein the cells comprise fibroblasts, iPS cells, hESC cells, or HEK 293 cells.

* * * * *